United States Patent [19]

Thompson et al.

[11] Patent Number: 4,817,016

[45] Date of Patent: Mar. 28, 1989

[54] NON-DESTRUCTIVE EVALUATION MEANS AND METHOD OF FLAW RECONSTRUCTION UTILIZING AN ULTRASONIC MULTI-VIEWING TRANSDUCER DATA ACQUISTION SYSTEM

[75] Inventors: Donald O. Thompson; Samuel J. Wormley, both of Ames, Iowa

[73] Assignee: Iowa State University Research Foundation, Inc., Ames, Iowa

[21] Appl. No.: 865,775

[22] Filed: May 21, 1986

[51] Int. Cl.$^4$ .............................................. G01N 29/04
[52] U.S. Cl. ...................................... 364/507; 73/598; 73/600; 73/602
[58] Field of Search .................. 73/598, 599, 600, 602, 73/607, 625, 627, 628; 364/507

[56] References Cited

U.S. PATENT DOCUMENTS

| | | | |
|---|---|---|---|
| 3,262,307 | 7/1963 | Hart | 73/629 |
| 3,280,621 | 10/1963 | Cardinal et al. | 73/625 |
| 3,910,124 | 10/1975 | Halsey | 73/607 X |
| 4,129,041 | 12/1978 | Bickel | 73/657 |
| 4,299,128 | 11/1981 | Gruber | 73/627 |
| 4,362,059 | 12/1982 | Zwyssig | 73/628 |
| 4,441,369 | 4/1984 | Lessard et al. | 73/602 |
| 4,475,394 | 10/1984 | Takeda et al. | 73/600 X |
| 4,571,529 | 2/1986 | Arita et al. | 73/602 X |
| 4,576,048 | 3/1986 | Glenn | 73/628 X |
| 4,682,497 | 7/ 87 | Sasaki | 73/628 X |

OTHER PUBLICATIONS

Thompson et al.; "Long & Intermediate Wavelength Flaw Reconstruction"; Proceedings of the Second Symposium on Energy Engineering Sciences, Apr. 10–11, 1984, pp. 86–93.

Thompson et al.; "Long & Intermediate Wavelength Flaw Reconstruction"; Review of Progress in Quantitative Nondestructive Evaluation; vol. 4A, 1985, pp. 287–296.

Hsu et al.; "Reconstruction of Inclusions in Solids Using Ultrasonic Born Inversion"; J. Appl. Phys., vol. 55, No. 1, Jan. 1984, pp. 162–166, 168.

Wormley et al.; "Error Sensitivity of Long & Intermediate Wavelength Flaw Reconstruction"; Review of Progress in Quantitative Nondestructive Evaluation; vol. 4A, 1985, pp. 203–211.

Hsu et al.; "Reliability of Reconstruction of Arbitrarily Oriented Flaws Using Multiview Transducers"; Ames Laboratory, 1986, pp. 1–14.

Rose, "Inverse Scattering at Long Wavelength", Proceedings of DARPA/AFML Review of Quantitative NDE Boulder, (1981), Plenum Press.

(List continued on next page.)

Primary Examiner—Parshotam S. Lall
Assistant Examiner—Edward R. Cosimano
Attorney, Agent, or Firm—Zarley McKee, Thomte, Voorhees & Sease

[57] ABSTRACT

A multi-viewing ultrasound transducer acquisition system for non-destructive evaluation, flaw detection and flaw reconstruction in materials. A multiple transducer assembly includes a central transducer surrounded by a plurality of perimeter transducers, each perimeter transducer having an axis of transmission which can be angularly oriented with respect to the axis of transmission of the central transducer to intersect the axis of transmission of the central transducer. A control apparatus automatically and remotely positions the transducer assembly with respect to the material by a positioning apparatus and adjusts the perimeter transducers with respect to the central transducer by an adjacent apparatus. The invention first determines the relative parameters of the material. The center and perimeter transducers and then positioned by instructions from the control apparatus in a desired position with regard to the material and adjusted with regard to each other so that the time paths for each transducer are equalized. The transducers are then operated individually, or in conjunction with all or any combination of each other, to transmit and/or receive ultrasonic waves. Flaw data is derived from the reflected ultrasonic waves. The flaw data is corrected to account for data deficiencies and then mathematical calculations are operated upon the data to identify and construct approximations of the flaws in the host material. These approximations of flaws are then documented for visual inspection and/or recordal.

10 Claims, 9 Drawing Sheets

OTHER PUBLICATIONS

Rose, Opsal, "Inversion of Ultrasonic Scattering Data", Proceedings DARPA/AMFL Review of Quantitative NDE Boulder, (1981), Plenum Press.

R. B. Thompson, D. O. Thompson, "New Techniques for Quantitative NDE, In Nondestructive Evaluation: Microstructural Characterization and Reliability Strategies", Buck and Wolf, Editors; The Metallurgical Society of AIME, Warrendale, Pa., 1981.

R. B. Thompson, D. O. Thompson, "NDE Programs at the Ames Laboratory and Iowa State University", In Quantitative NDE in the Nuclear Industry, Clough, Editor; American Society for Metals, Metals Park, Ohio, 1983.

D. O. Thompson, Wormley, Rose and R. B. Thompson, "Elastic Wave Scattering from Multiple Voids (Porosity)", Review of Progress Quantitative Nondestructive Evaluation, vol. 2A, pp. 867–882, Plenum Publishing Corp., 1983.

Frazier, "Finding the Fatal Flaw", Mosaic, Sep./Oct., 1983, pp. 28–36.

Van, "Technology Focuses on Fatal Flaws", Chicago Tribune, Sec. 6, Mar. 25, 1984.

R. B. Thompson, D. O. Thompson, H. M. Burte, D. E. Chimenti, "Use of Field-Flaw Interaction Theories to Quantify and Improve Inspection Reliability", Review of Progress in Quantitative NDE, vol. 3, D. O. Thompson and Chimenti, Editors; Plenum Publishing, New York, 1984.

Rose, "Elastic Wave Inverse Scattering in Non-Destructive Evaluation".

R. B. Thompson and T. A. Gray, "Range of Applicability of Inversion Algorithms", pp. 233–244.

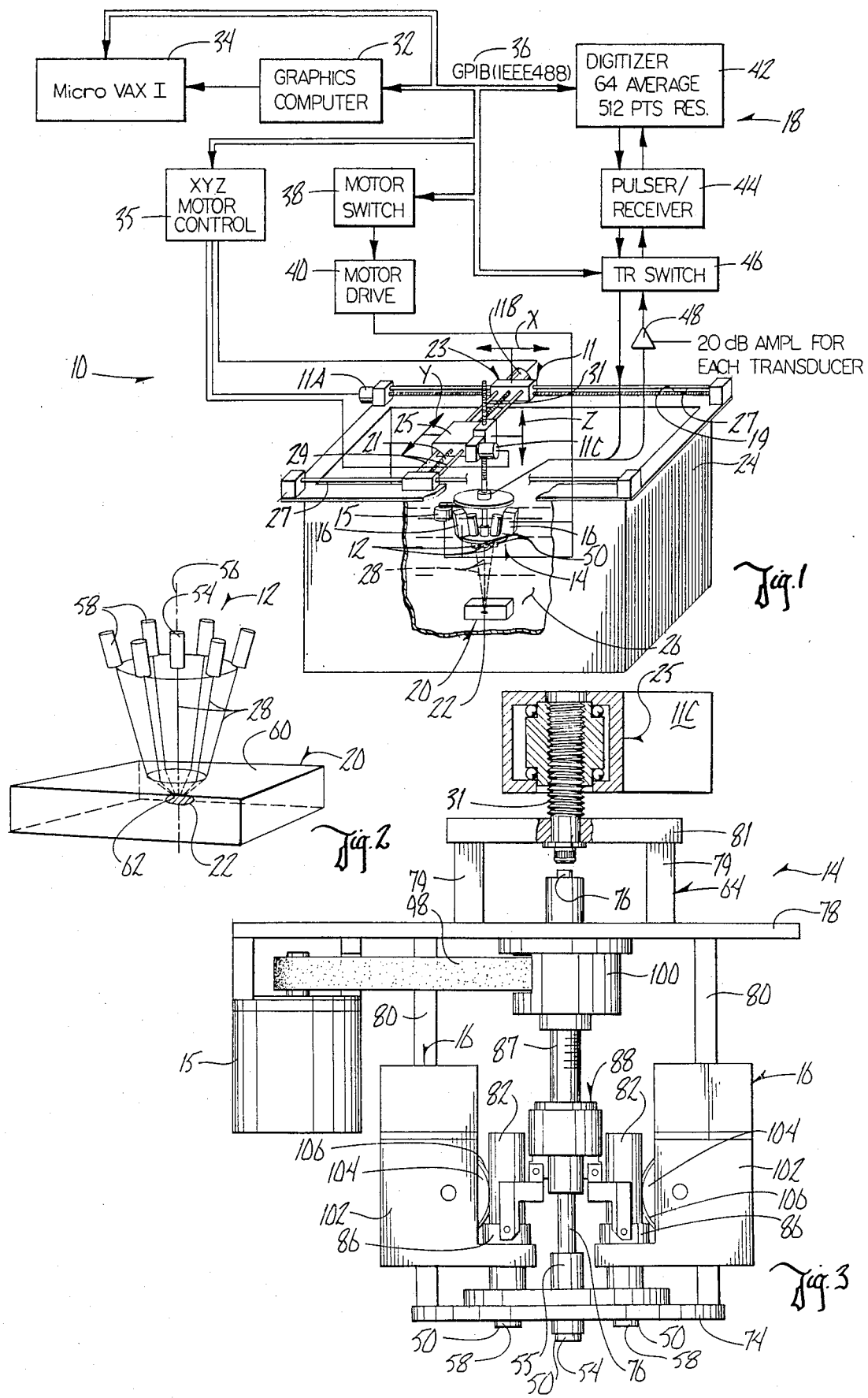

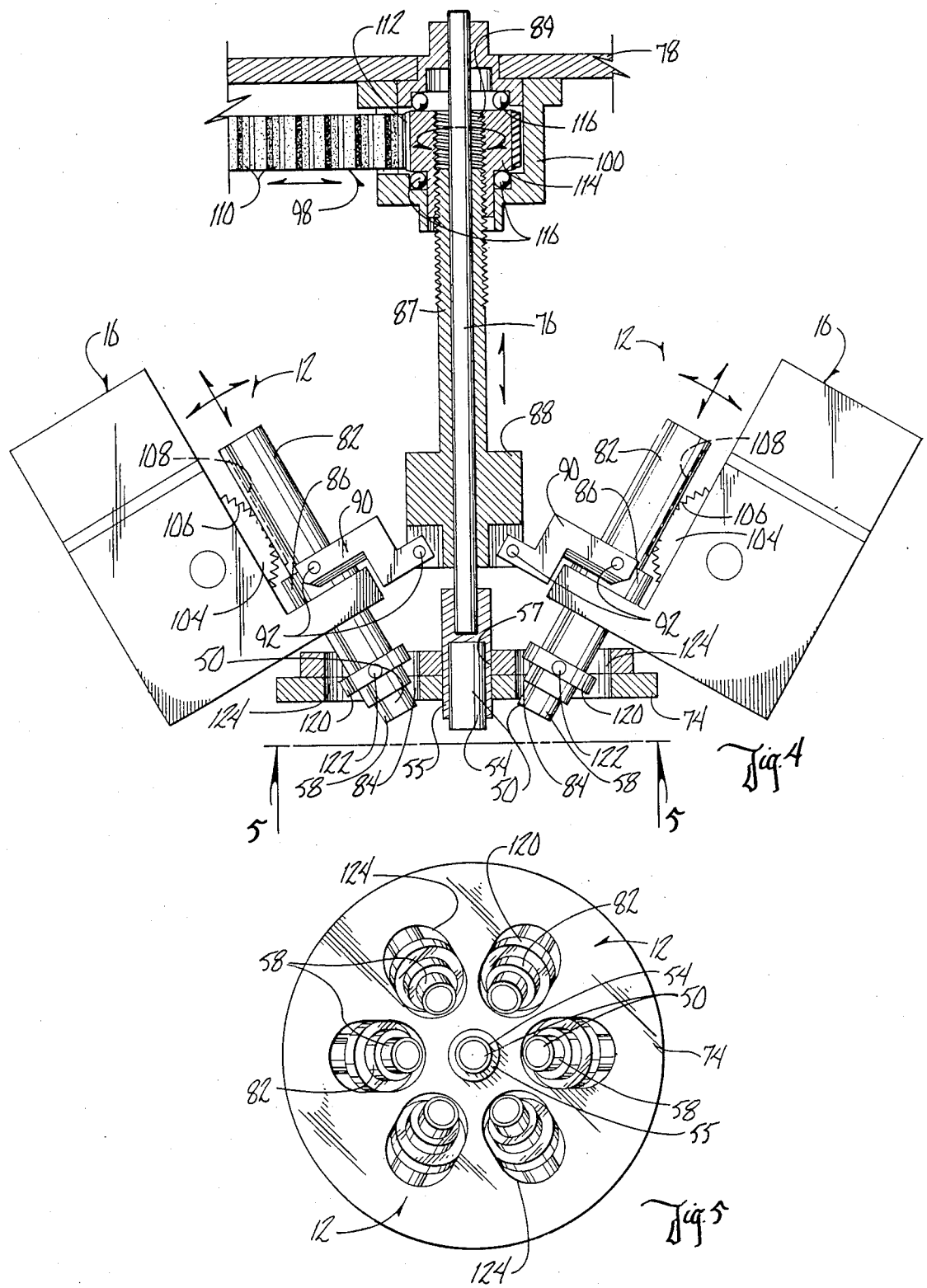

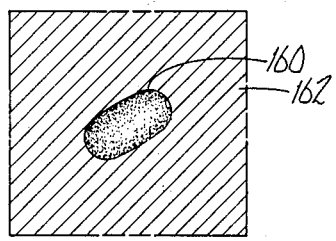
Fig. 10
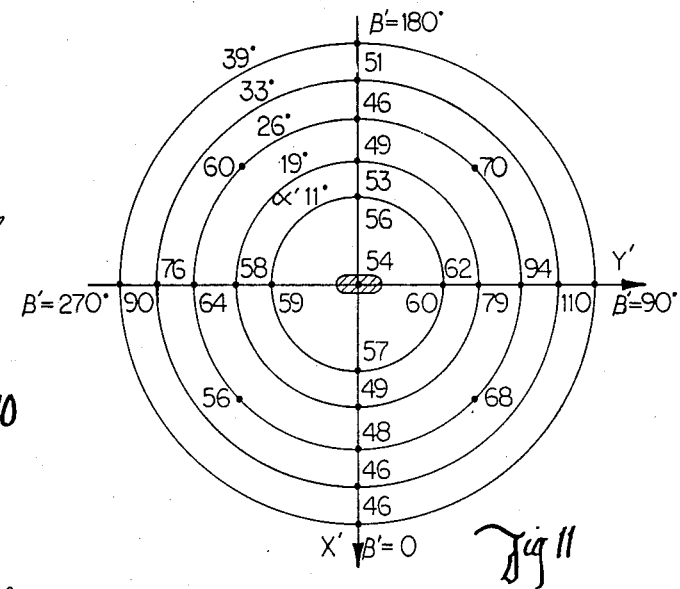
Fig. 11
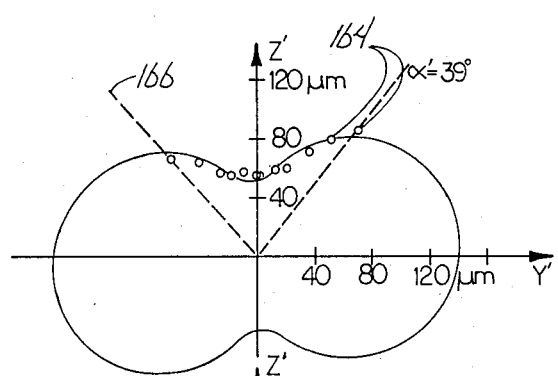
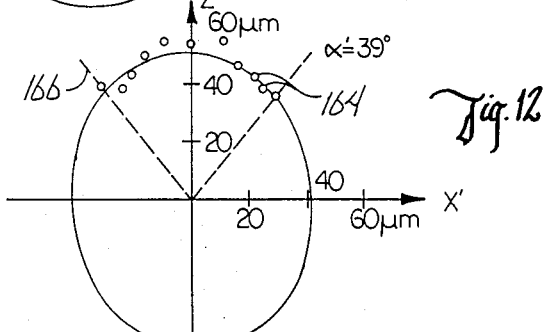
Fig. 12
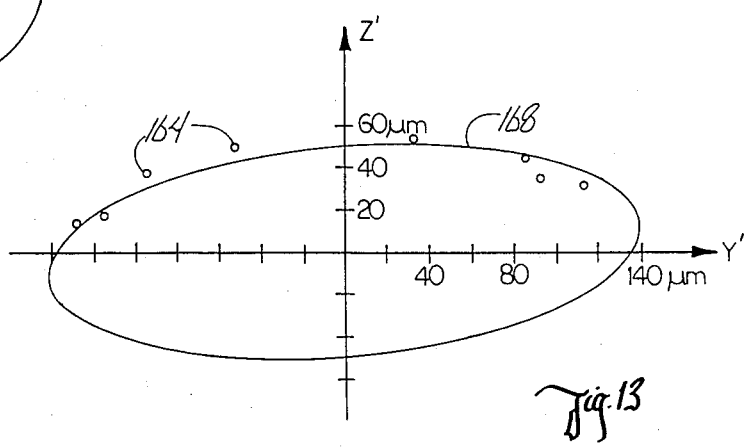
Fig. 13

ELLIPSOID PERSPECTIVE PLOT: 80°, 10°
Experiment (400,380,194,-36,73,29)

NON-DESTRUCTIVE EVALUATION MEANS AND METHOD OF FLAW RECONSTRUCTION UTILIZING AN ULTRASONIC MULTI-VIEWING TRANSDUCER DATA ACQUISTION SYSTEM

GRANT REFERENCE

This invention was conceived and reduced to practice at least in part under a grant from the Department of Energy under Contract No. W-7407-ENG-82.

REFERENCE TO MICROFICHE APPENDIX

Appended to this specification is a microfiche appendix of an embodiment of the software programming utilized with the invention. The microfiche appendix consists of nine microfiche pages containing a total of 353 frames.

BACKGROUND OF THE INVENTION

1. Field of the Invention

This invention relates to a means and method for nondestructive evaluation of flaws in a host material by utilizing the data derived from ultrasonic transducers, and in particular, relates to flaw reconstruction utilizing an ultrasonic multiviewing transducer data acquisition system in the long and intermediate wave lengths.

2. Problems in the Art

Knowledge of flaws and related properties of materials is of extraordinary value. Accurate information of that kind, especially with regard to materials which are used in high stress or safety sensitive applications, provides maintenance and inspection personnel with the ability to reject, repair, or replace the materials or parts which are subject to failure, thereby averting damage or even loss of life.

One method of attempting to obtain flaw information involves taking portions of the material and breaking it down to analyze its properties and to identify characteristic flaws. The obvious shortcoming of this method is that it does not allow evaluation of materials in existing use (it is destructive as compared with non-destructive), and only would give an estimate of material properties for prediction of possible later forming flaws.

Therefore, methods of flaw evaluation were developed which allow unlimited and possibly even in-use analysis of materials (non-destructive evaluation). Non-destructive evaluation (NDE) does not require "destruction" or alteration of the part or material in order to derive information concerning flaws therein. Currently, there are many different forms and methods of NDE including, but not limited to, such different procedures as ultrasonic waves, electromagnetic eddy currents, thermal wave imaging, nuclear magnetic resonance (NMR), and x-ray technologies.

An illustrative example of the advantages of NDE is as follows. Turbine fan blades for jet aircraft engines are under tremendous forces and stresses during operation, and are critical to the continuing operation of the engine. Because of the critical nature of these parts, and the knowledge that a very small percentage fail due to inherent flaws after a certain period of time, all of these parts are replaced and discarded after the minimum period of time. Unfortunately, most of the other blades would have useful lives of up to ten times the life span which they are actually used. NDE now allows the parts to be screened so that the small percentage which probably would fail can be detected during routine maintenance and discarded, whereas those parts not exhibiting the flaw characteristics could continue to be used, saving tremendous amounts of money. It has been estimated that for one particular type of jet engine alone currently being used, annual savings would run into the tens of millions of dollars.

While NDE is very promising from the standpoints of economy and safety, no NDE system has yet been developed which can consistently, accurately, and efficiently analyze and identify flaws of all types and shapes to the extent necessary to achieve the desired accuracy demanded by industry and the military. There is a real need for an NDE system which accurately can derive size, shape, location, and orientation of flaws.

Electromagnetic eddy current NDE systems are restricted to near surface flaws in materials. Thermal wave imaging NDE systems cause heating of the material being tested. NDE and x-ray technologies are very high in cost and are not generally cost-effective for broad applications.

Current ultrasound technology utilizes various methods itself. All are based on interrogating the material being studied by introducing ultrasonic waves into the material and then analyzing the reflected waves coming back to derive the desired flaw data. Some systems utilize one transducer which sends and receives ultrasound energy whereas other systems utilize multiple transducers. In fact, one method utilizes hundreds of transducers in an effort to attempt to construct a three dimensional image of the flaws.

The present ultrasonic NDE methods are deficient in that they either are not able to accurately identify and reconstruct the flaws, are unable to derive the required information to be beneficial, or utilize such complex structure to make it uneconomical or impractical.

Therefore a real need exists for an NDE method and means for reconstruction of flaws which accurately identifies and reconstructs the size, shape, and orientation of flaws in the material, while additionally avoiding the requirement of physically scanning the flaw and using much higher frequencies which exhibit increased problems with attenuation.

It is therefore a primary object of the invention to improve over and solve the problems and deficiencies in the art.

A further object of the invention is to provide a means and method for reconstruction of flaws in materials which accurately identifies and reconstructs the size, shape, and orientation of the flaws.

A further object of the invention is to provide a means and method for acquiring flaw data which takes into account and corrects attenuation, diffraction and interface losses of the material, and any problems involved herewith.

Another object of the invention is to provide a means and method for flaw reconstruction which allows for multiple viewing options for the ultrasonic transducers according to desire.

Another object of the invention is to provide a means and method for flaw reconstruction which can utilize long and intermediate wave lengths of ultrasound to accomplish the same.

A further object of the invention is to provide a means and method of flaw reconstruction which allows for automatic and remote control of the adjustment of the ultrasound transducers so that their time paths are equalized and this equalization can be maintained.

A further object of this invention is to provide a means and method for flaw reconstruction which utilizes a plurality of transducers.

Another object of the invention is to provide a means and method for flaw reconstruction which can produce a three dimensional model of the flaws in the materials and can provide documentation and visualization of the same.

A further object of the invention is to provide a means and method of reconstruction of flaws which combines the system of deriving flaw data utilizing ultrasound, with computer means and software programming means to automatically control the positioning and adjustment of the transducers and to mathematically operate upon the derived flaw data from the transducers to identify and reconstruct flaws in the material.

Further objects, features, and advantages of the invention will become apparent with reference to the accompanying specification and drawings.

SUMMARY OF THE INVENTION

The present invention utilizes a plurality of ultrasonic transducers to derive flaw data from the material being analyzed. The transducers include a central transducer with a plurality of perimeter transducers encircling the the central transducer. The perimeter transducers are angularly disposed and adjustable with respect to the central transducer so that the axes of transmission of the perimeter tranducers intersect that of the central transducer.

An adjustment means and a positioning means are automatically controllable by an operator to first, adjust the perimeter transducers' axes of transmission with respect to the host material and with respect to the axis of transmission of the central transducer according to desire. Secondly, the perimeter transducers are adjustable along their axes of transmission so that the time paths for each can be equalized to high precision.

A computer, including computer programming software, is connected to the transducers and is programmed to operate upon the flaw data information contained in the ultrasonic reflections or back scatter received by any of the transducers. The computer programming operates on this data to correct problems concerning attenuation, diffraction, losses at the interfaces, and deconvolution. The computer extracts flaw surface-to-centroid radius estimates for each back scatter signal using a one dimensional (1D) inversion Born approximation. It then applies mathematical operations and analysis to construct a three dimensional model of the flaws in the material. Finally, the programming allows the models of the flaws to be visually represented and documented.

Potential uses for the invention include inspection of airplanes, nuclear reactors, energy containment systems, and undersea structures. Additional advantageous use can be foreseen in such areas as automobile manufacturing, metal-producing industries, and manufacturing generally, as an on-line, non-destructive evaluating tool which identifies and reconstructs flaws and then determines if they are endangering or benign.

BRIEF DESCRIPTION OF THE DRAWINGS

FIG. 1 is a partial perspective, partial schematic view of the invention including a depiction of the host material being interrogated, the mechanisms for vertical and horizontal positioning of the transducer array, and the operating environment of the invention.

FIG. 2 is a schematic representation depicting the preferred arrangement of transducers according to the invention, and depicting their orientation to a host material having a flaw being interrogated.

FIG. 3 is a front elevational view of the transducer array assembly showing a central transducer and two perimeter transducers and the mechanism for positioning the transducer array vertically to the host material.

FIG. 4 is a partial sectional front elevational view similar to FIG. 3 showing the adjustment mechanisms for changing the angular orientation of the perimeter transducers, with respect to the host material and with respect to one another, and for changing the position of each perimeter transducer along its transmission axis.

FIG. 5 is a bottom plan view of the preferred arrangement of the transducers, according to the invention.

FIG. 10 is a cross-sectional elevational view of an example of a flaw in a host material.

FIGS. 11–18 are illustrations of the operations which are performed and the models of flaws which are derived from the system according to the invention.

DETAILED DESCRIPTION OF THE PREFERRED EMBODIMENT

Figure 6:
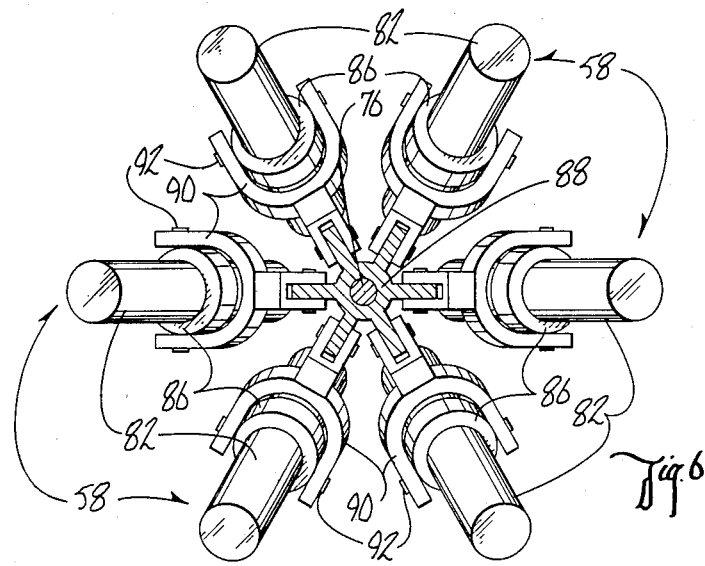
FIG. 6 is an isolated top plan view of the preferred transducer array according to the invention.

With reference to the drawings, and particularly FIG. 1, the preferred embodiment of the invention will now be described. The invention 10, being a comprehensive means and method for detecting and reconstructing flaws in what will be called host materials 20, includes in its preferred embodiment a plurality of ultrasonic transducers 12 adjustably mounted in a transducer assembly 14. Transducer assembly 14 can be accurately positioned vertically and horizontally with respect to the host material 20 by utilizing xyz bridge positioner 11, such as is known in the art. Electronic assembly 18 instructs the operation of xyz bridge positioner 11 and transducers 12, mathematically operates on the multiplexed information derived from transducers 12, and from these mathematical operations derives a reconstructed model of the flaw or flaws.

As can be seen in FIG. 1, the preferred method for interrogation of host material 20 for flaw(s) 22 is to position host material 20 within a holding tank 24 containing a liquid medium 26, which in this case is water. Positioning of transducer assembly 14 by xyz bridge positioner assembly 11 is accomplished as follows. Movement in the horizontal plane is accomplished by the operation of stepping motors 11a ("x" movement) and 11b ("y" movement), which simply are directly connected to ball screws 19 and 21 respectively, which move cross-assembly 23 and/or carriage 25 along rails 27 and 29 according to command. Stepping motor 11c is used in combination with ball screw 31, as will be explained below, to raise or lower ("z" direction) transducer assembly 14 into liquid medium 26 so that transducers 12 are submersed therein, to facilitate the efficient operation of ultrasonic transmission and reception and then to accurately vertically position transducers 12 with respect to host material 20. Stepping motors 11a, 11b and 11c allow vertical and horizontal scanning of a host material 20 by moving transducer assembly 14 with respect to host material 20. The procedure of positioning the host material and transducers within a liquid medium and with respect to a host material is well known within the art. Arrows x, y and z illustrate the ability of the invention to move transducer assembly 14 in any direction with respect to host material 20.

As can be further noted in FIG. 1, transducers 12 are generally oriented in such a manner to one another that their axes of transmission 28 converge generally to intersect approximately at the location of flaw 22. As will be further discussed below, transducers 12 are adjustable both in their angular orientation to one another and along their axes of transmission 28, these adjustments being accomplished by structure associated with stepping motors 15 and 16.

Electronic assembly 18 is schematically portrayed in FIG. 1 and includes the electronic circuitry, electronic components, computers, and attendant software described below. The overall control of the system and the mathematical operations performed on the multiplexed transducer data are controlled by computer. It is to be understood that the coarse positioning of transducer assembly 14 into holding tank 24 and with respect to host material 20 can be accomplished by control of stepping motors 11a, 11b, and 11c by either computer or manually, but that exact positioning according to requirements for particular application are best accomplished by automatic computer control of the positioning of transducer assembly 14. In the preferred embodiment, xyz bridge positioner 11 is a Testech Model MBT-200 Series Positioning Bridge and Tank Assembly (available from Testech, Inc., Exton, Pa.) which accomplishes the positioning of assembly 14 according to instruction from computers 32 and/or 34 channeled through IEEE 488 bus 36 and xyz motor control 35 to servo motors 11a, 11b, and 11c. Xyz motor control 35, in the preferred embodiment, is a programmable xyz drive system made by Klinger Scientific, 110-20 Jamaica Ave., Richmond Hill, N.Y. 11418, having a model number of CC1.1 and CC1.2.

The ultrasonic transducers 12 are utilized to, first, detect flaws in host material 20, and then focus on the flaw 22 to derive its reconstruction. The array of transducers (see FIG. 2) used in the preferred embodiment thus requires two types of movement. Depending on the vertical height of transducers 12 from the flaw 22 and the exact point at which the axes of transmission of transducers 12 are desired to be focused, the angular orientation of perimeter transducers 58 towards central transducer 54 must be adjusted (see FIG. 2). This is accomplished by interconnection of all perimeter transducers 58 to an adjustment assembly controlled by a single drive (servo motor 15), which eliminates individually adjusting each perimeter transducer 58. A second movement of perimeter transducers 58 involves adjustment of each transducer 58 along its axis of transmission, this being performed by an assembly associated with a servo motor 16 for each perimeter transducer 58. These functions and structure will be described in more detail below. In the preferred embodiment, either graphics computer 32, being in communication with a main frame computer 34, or the main frame computer 34, interfaces the desired commands to servo motors 15 and 16 through GPIB (General Purpose Interface Bus) IEEE 488 (reference numeral 36) directed through motor switch 38 and motor drive 40. Motor switch 38, upon command, instructs motor drive 40 to operate stepping motor 15 to angularly orient perimeter transducers 58 with respect to one another and to central transducer 54, and can operate stepping motors 16 for each transducer 12 which needs to be axially adjusted to equalize their ultrasonic time paths with respect to the other transducers 12. These operations will be discussed in detail below.

The operation of transducers 12, and the receipt and processing of the data received by transducers 12 is accomplished by the components to the right side of electronic assembly 18 in FIG. 1. A digitizer 42 is directly connected to computers 32 and 34 via bus 36 and communicates with pulser/receiver 44. Pulser/receiver 44 is in turn communicated with transducer selector switch 46 (TR switch) which also is directly communicated with computers 32 and 34 by bus 36. TR switch 46 is also directly communicated with each transducer 12. The signals received from transducers 12 are passed through amplifiers 48 (for each transducer) before entering TR switch 46.

It is to be understood that the present system allows computers 32, 34 to operate transducers 12 in a plurality of different manners to derive different information. The circuitry also serves to avoid cross-talk and interaction between transducers 12. For example, each transducer 12 can be individually pulsed in any sequence, or any number of transducers 12 can be simultaneously pulsed. Moreover, the transducers 12 can be operated in different modes, such as pitch catch, or pulse-echo. All of these various methods are known within the art. The primary feature, however, of the present invention is that with the plurality of transducers 12, each is individually operable to allow it to be controlled individually and/or simultaneously with the others. Each transducer 12, of course, can also receive ultrasonic signals, either from itself, or from any other transducer 12.

Therefore, as can be seen in FIG. 1, TR switch 46 is first instructed as to which transducers 12 will be operated, and in what sequence. Pulser/receiver 44 is then instructed to operate transducers 12 accordingly to pulse ultrasonic energy, and/or receive the same, in the desired sequence. Transducers 12 have already been positioned as desired and therefore the information received in the designated transducers 12 is boosted by amplifier(s) 48, channeled through TR switch 46, and passed to digitizer 42 which digitizes the information for use with graphics and/or main frame computers 32 and 34. The information is therefore in a form which can be operated on according to the methods of the invention to derive the model of flaw(s) 22.

In the preferred embodiment, transducers 12 are Panametrics V3404 10/0.25 piezo electric transducers available from Panametrics, 221 Crescent St., Walthem, Mass. 02254. Transducers 12 can operate in any pulse/receive mode as is conventional to them, including pitch-catch and pulse-echo. Transducers 12 are operated in the long and intermediate wavelengths on the order of flaw size (high frequency) and are a phased and focused sparse array, which allows derivation of a maximum amount of information about flaw(s) 22 with a minimum amount of data acquisition and processing. Transducer cables 50 are Panametrics BNC-to-microdot transducer cables which help avoid cross-talk and interaction between transducers 12 whereas pulser/receiver 44 is a Panametrics 5052PR pulser/receiver, both available from Panametrics.

The power supply (not shown) for the 20 dB amps (48) is ±15 volts and, as is known in the art, can be supplied by any suitable means known in the art.

Stepping motors 11a, 11b, and 11c are available from Shinkoh Communication Ind., Co., Japan, under a product named and numbered Astrosyn 23PM-C109, being powered by 5.4 vDC and being moveable by 1.8° per step, such as is known and available in the art. Stepping motors 15 and 16 are comprised of Model Number KP6M2-002, 12 vDC, stepping motors manufactured and available from Japan Servo Company, Ltd., Tokyo, Japan. As mentioned above, stepping motor 15 controls the angular orientation of transducers 12 to one another, while stepping motors 16 individually adjust transducers 12 along their axes to alter and adjust their ultrasonic time paths.

Holding tank 24 is made by Testech, Inc. of Exton, Pa. 91341. While water is the preferred liquid medium 26, other liquids (e.g. glycerin, liquid gallium), such as are known in the art, would also suffice.

Graphics computer 32 is a Tektronix 4052A graphics computer with a 64K memory. It is to be understood that it could also include a Tektronix Optional 28 Extended Memory. Mainframe computer 34 is preferably a DEC MicroVAX I or II system with a 20 megabyte disc storage. Alternatively, it could be a YAX 11/70 with similar storage.

Bus 36, designated in FIG. 1 as GPIB (IEEE 488), can be any suitable electronic connection bus as is known in the art. In the preferred embodiment a Hewlett-Packard IEEE 488 Bus (industry standard) is used.

Motor switch 38 is preferred to include a Textronix MI5010 programmable interface, a Textronix 50M40 Relay Scanner, and a Textronix TM5003 Main Frame component directly in electrical communication with motor drive 40 which can be any suitable electronically controlled motor for controlling stepping motors 16. Motor drive 40 is conventional in the art and interfaces motor switch 38 with servo motors 15 and 16. In the preferred embodiment motor drive 40 was constructed in-house, and can be done so by one ordinarily skilled in the art.

Digitizer 42 includes a Textronix 7912AD digitizer having 64 average and 512 points resolution, a Textronix 7B92A dual time base, a Textronix 7A16P Programmable Amplifier, and optionally can include an NEC video character display having a model number of JB-1201M(A).

Pulser/receiver 44 is the Panametrics 5052PR pulser/receiver. Transducer/selector switch 46 includes a Textronix 5010 Programmable Scanner and a Textronix TM 5003 Main Frame component. Amplifiers 48 are Comlinear E 103-N-BNC-50-50-4020 dB Amplifiers having a range from DC to 150 Mhz.

It is thus to be understood that the general operation of the invention 10 is to first place host material 20 within liquid medium 26 in holding tank 24. XYZ motor control 35 directs stepping motors 11a, 11b, and 11c by instructions from computers 32 and/or 34 to position transducer assembly 14 in such a way as to place transducers 12 within liquid medium 26 at a desired position with relation to host material 20. Stepping motor 15 is then operated to orient the angular attitude of the axes of transmissions 28 of perimeter transducers 58 to converge with the axis of transmission of central transducer 54 upon the desired location on host material 20 for interrogation of host material 20. In the preferred embodiment, perimeter transducers 58 can be set, as a group, anywhere between 0° and 30° at ±1/8° with respect to the normally incident central transducer 54. Additionally, it is to be understood that a testing sequence goes on in the system to automatically tell the computers if transducers 12 are properly oriented with one another. Also, once transducers 12 are positioned in approximately the right position, a further sequence can be performed by computers 32 and 34 to insure that the time paths for each transducer 12 are exactly equal. This operation includes operating stepping motors 16 to minutely adjust transducers 12 along their axes of transmission 28 to insure the equivalent time paths. Once the above steps are accomplished, electronic assembly 18 is operated according to graphics and/or mainframe computers 32 and 34 to instruct the pulsing and reception of ultrasonic signals for transducers 12 to interrogate and receive back information from host material 20 which then can be processed to derive the reconstruction of flaws 22 in host material 20.

FIG. 2 specifically shows schematically the preferred array of transducers 12 for the invention 10. As can be seen, a fixed central transducer 54 is positioned so that its axis of transmission 28 is co-linear with the vertical axis 56 of the array generally. Six perimeter transducers 58 are angularly disposed radially around central transducer 54. Each perimeter transducer 58 is angularly adjustable with respect to vertical axis 56 in such a manner that each axes of transmission 28 of each perimeter transducer 58 is intersectable with vertical axis 56, which is the axis of transmission of central transducer 54.

As can be seen in FIG. 2, array of transducers 12 is positioned with respect to host material 20 in such a manner that the axes of transmission 28 of perimeter transducers 58 and central transducer 54 intersect and converge at flaw 22. As is known in the art, the axes of transmissions 28 are refracted at the surface 60 of host material 20. By selectively pulsing and receiving, in sequence, various of the transducers 12, different information can be obtained concerning flaw 22, in effect, producing a three dimensional reconstruction of flaw 22. It is to be understood that once transducers 12 are positioned so as to detect flaw 22 (by scanning along the host sample 20), the sparse array of transducers 12 are used to reconstruct the flaw. This is accomplished by aligning transducers 12, which means that the correct angles are set for the given distance of the transducers 12 from flaw 22 so that beams from all transducers intersect at the position of the flaw. It is to be further understood that for additional viewing angles, the array of transducers 12 can be moved vertically closer or further away from the flaw 22 and then the angles reset on flaw 22. One set of information is generally sufficient; however, three dimensional reconstruction of flaws may require a number of different viewing positions. At one viewing position nineteen view readings are generally taken.

Although it is not essential for the operation of the invention that the time paths for each perimeter transducer 58 be exactly identical, the present invention does include this additional capability so that variances in the density or other properties of the host material 20 can be detected. For the time paths to be essentially equivalent for all axes of transmission 28 simply means that each perimeter transducer 58 must be adjusted along its axis of transmission 28 so that the time it takes ultrasonic energy to reach convergence point 62 at flaw 22 and the return to its eminating perimeter transducer 58 must be equal for each perimeter transducer 58 and for central transducer 54. This being accomplished, any combination of pulse and reception between any two transducers 12 will provide accurate information concerning flaw 22, thus facilitating the "3D" like reconstruction made possible by invention.

FIGS. 3 and 4 depict the exact structural components of the transducer assembly 14, in the preferred embodiment. A framework 64 supports transducer assembly 14 including transducers 12, stepping motors 15 and 16, and the mechanisms for adjusting angular orientation and axially position of perimeter transducers 58. As can be seen, the attachment of framework 64 of transducer assembly 14 to carriage 25 of xyz bridge positioner 11 is accomplished by simply attaching ball screw 31 to framework 64 by any means known in the art. Transducer assembly 14 is vertically raised or lowered in response to movement of ball screw 31 according to desire. This raising or lowering can either be controlled by stepping motor 11c taking instructions from computers 32 and 34, or can be manually done. It is to be understood that many means and methods for controlling vertical and horizontal movement of transducer assembly 14 are known and could be used to achieve this result within the art. It is preferred that such a system, as is well known within the art, be precisely computer controllable to allow precise scanning across and positioning to host material 20.

Transducers 12 are connected to framework 64 at its lower end as shown in FIGS. 3 and 4. Face plate 74 is horizontally disposed at the bottom of framework 64. Central transducer 54 is mounted in the lower end of central transducer mount 55 which is secured in aperature 57 through the center of face plate 74. A stationary support rod 76 is secured between the upper end of central transducer mount 55 and middle support plate 78. Vertical support bars 80 extend between base plate 74 and middle support plate 78. Upper mounting bars 79 and plate 81 are utilized with respect to attachment to ball screw 31.

Central transducer 54 is secured to the bottom of base plate 74 in colinear alignment directly with central support rod 76. Perimeter transducers 58 are connected to the lower ends of perimeter transducer adjustment tubes 82 which extend through corresponding aperatures 84 in face plate 74. It is to be understood that in FIGS. 3 and 4, only two perimeter transducers 58 are shown for purposes of clarity. However, the same structure and operation apply to each of the six perimeter transducers 58 in the preferred embodiment (see FIG. 2).

Each perimeter transducer adjustment tube 82 in turn is journalled in a sleeve 86 which is hingeably secured to carriage 88 by brackets 90. Brackets 90 are hingeably interconnected between sleeves 86 and carriage 88 by hinge pins 92.

Carriage 88 is vertically adjustable and slideable along central support rod 76. The upper portion 87 of carriage 88 is threaded to mate with the threaded interior bore 89 of rotatable gear 114. Rotatable gear 114 is rotatable between ball bearings 116 disposed between gear 114 and gear housing 100.

Stepping motor 15, secured to plate 78 of framework 64, translates rotational motion via notched timing belt 98 to rotatable gear 114. Rotation of rotatable gear 114 via belt 98 in turn causes carriage 88 to move upwardly or downwardly depending upon threading and direction of rotation of rotatable gear 114. Movement of carriage 88 causes concurrent angular movement of perimeter transducers 58 because of their hinged connection by brackets 90. Upward movement of carriage 88 causes divergence of the axes of transmission 28 of perimeter transducers 58, while downward movement of carriage 88 causes increasing convergence of the same.

It can also be seen in FIGS. 3 and 4 that stepping motors 16 are positioned adjacent to each perimeter transducer 58, secured in place around sleeves 86. Each stepping motor 16 contains a pinion gear or drive wheel 104 having gear teeth 106 along its perimeter. Reference numeral 102 refers to the housing for attaining rotatable drive wheel 104.

Each perimeter transducer adjustment tube 82 has a corresponding rack or toothed track 108 which mates with gear teeth 106 of drive wheel 104. Therefore, operation of each stepping motor 16 causes corresponding perimeter tranducer adjustment tube 82 to move axially in sleeve 86 thereby adjusting corresponding perimeter transducer 58 along its axis of transmission 28.

FIG. 4 shows, by sectional view, that belt 98 has ribs 110 which mate with slots 112 in gear 114 which is rotatably held within gear housing 100 by bearings 116. Belt 98, with its raised ribs 110 which fit within slots or grooves 112 in the rotatable gear 114, therefore drives the rotation of gear 114 which raises or lowers carriage 88, to in turn simultaneously adjust the angular orientation of perimeter transducers 58. Gear housing 100 is secured to central support rod 76 and plate 78. Furthermore, it can be seen that the lower end of perimeter transducer adjustment tubes 82 are gimbal-mounted in ring mounts 120 hinged on hinge pins 122 within apertures 124 in base plate 74. Ring mounts 120 are secured to adjustment tubes 82, and hinge pins 122 are in turn secured to ring mounts 120. Hinge pins 122 extend into apertures (not shown) in base plate 74 to allow the hinging movement of perimeter transducers 58. As can be seen in FIG. 5, the perimeter transducers 58 extend below and through apertures 124 in base plate 74.

FIG. 4 also shows, in comparison to FIG. 3, carriage 88 in a downward position which causes perimeter transducer adjustment tubes 82 to angle inward thus converging the axes of transmission 28 of perimeter transducers 58 almost directly below the bottom end of central transducer 54.

FIG. 5 depicts the array of transducers 12 as they would be seen from a bottom view of base plate 74 in the position shown in FIG. 4. The array of transducers 12 converge to allow focused multiple angled views of flaw 22.

FIG. 6 depicts an isolated view of what the array of transducers 12 would look like from the top in their position of FIG. 4. It can be seen that in the preferred embodiment, brackets 90 are basically U-shaped gimbal mounts to provide a stable, secure hinged mount for perimeter transducers 58, and that each perimeter transducer 58 is equally spaced around carriage 88.

Operation of the invention has three separate operating procedures; initialization, data acquisition, and mathematical flaw reconstruction. Initialization includes determining the properties of both the host material 20 and liquid medium 26. By referring to FIG. 7 a schematic depiction of some of the initialization parameters is shown. As can be seen, the axes of transmission 28 for central transducer 54 and perimeter transducers 58 converge and meet at flaw 22. Assuming that $D_W$ (distance between transducer and water) and $D_F$ (distance to the flaw from host material 20 surface) are known, the angle $\alpha$ at which the perimeter transducers 58 must be set with respect to the normal line 128 to host material 20 can be determined from the following equation:

$$\sin \alpha = \frac{v_w}{v_m} \sin \left\{ \tan^{-1} \left[ \frac{r_o - (D_T^{(1)} + D_w^{(1)}) \tan \alpha}{D_F} \right] \right\}$$

where $v_w$ = acoustic velocity in water
$v_m$ = acoustic velocity in sample host material 20
$D_T$ = Distance between end of central transducer and its pivot point
$r_o$ = Distance between center line and perimeter transducer pivot point Therefore, as is obvious, the acoustic velocities $v_w$ and $v_m$ must be determined as part of the initialization procedure. Other initialization procedures are described below.

Figure 7:
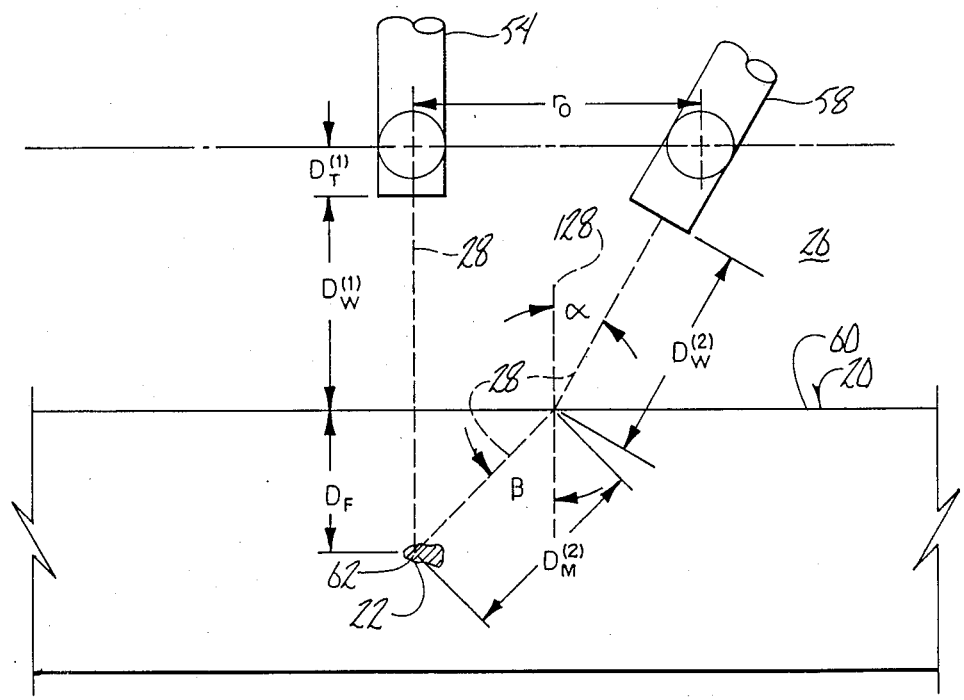
FIG. 7 is a schematic view showing the central transducer and one perimeter transducer, and their co-action in interrogating a flaw in a host material.

FIG. 7 therefore illustrates the various parameters involved in positioning central transducer 54, and each of the perimeter tranducers 58 with respect to a flow. FIG. 7 depicts one perimeter transducer 58 with respect to central transducer 54. The relationships shown in FIG. 7 are utilized to enable computer 34 to couple and then control positioning and adjustment of the transducer assembly 14 and all individual transducers with respect to the host material 20 and flaw 22 therein. All angles and distances are the same for other perimeter transducers 58 which might be utilized. It is further to be understood that distance $D_M^{(2)}$ represents the distance from the surface of the water to the flaw with respect to perimeter transducer 58. Angle $\alpha$ represents the angle between the axis of transmission 28 from perimeter transducer 58 and normal line 128 to the surface of the water. Angle $\beta$ differs from angle $\alpha$ by factoring in the defraction of the axis of transmission 28 caused by host material 20. This defraction factor is known, or can be derived, for any given host material. Angle $\alpha$ is known as the angle of incidence, whereas angle $\beta$ is the angle of refraction. Angle $\alpha$ is related to angle $\beta$ by Snell's law, and distance $D_M^{(2)}$ can be derived by simple geometry.

Any change in distance $D_W^{(1)}$ would require a change in angle $\alpha$ Likewise, $\beta$ would change according to the defraction characteristics of different host materials.

Data acquisition includes utilizing the plurality of transducers 12 to present a focused sparse array of long wavelength ultrasonic transducers which interrogate host material 20 to first locate a flaw 22, and then inspect it to derive enough information to mathematically reconstruct and document its size, orientation, location, and shape.

Table 1 below presents a sequenced chart of the general steps of the method of the invention as implemented by the means of the invention.

TABLE 1

Multiviewing Transducer Data Acquisition System

1. Input/edit Experiment Parameters (Velocity, Attenuation, etc.) (M1, M12, M13, M14)
2. Normal Incident Set-up and Alignment (Reference, Set Angle, etc.) (M2, M22)
3. Data Acquisition → FLAW(i) (M3, M31, M32, M33)
4. Thompson-Gray Measurement Model → SCA(i) (Attenuation, Diffraction, etc.) (M4, M44)
5. 1-D Inverse Born → Re(i) (M5) on MicroVax
6. Impulse Response Area Function (M6) on MicroVax
7. Regression Analysis Cl-C7 (M7) on MicroVax
8. Flaw Reconstruction & Identification (Display Regression Results) (M8, M81, M82)
9. Documentation of waveforms (M9)

Step 1—Input/Edit Parameters. As previously explained, the velocity of sound in the host material 20, as well as other fixed constants of the composite transducer inspection geometry, are required as input parameters to the system. Such parameters include accoustic velocity in water, accoustic velocity in the sample host material 20, attenuation, relevant distances and angles, and the like. Such initialization parameters are conventional as is known in the art.

Step 2—Normal Incident Allignment. The second part of the initialization procedure includes detecting a flaw 22 in host material 20 and then setting the desired angles of perimeter transducers 58, and equalizing their time paths. Flaws 22 are detected by deriving a flaw signal by utilizing the central transducer probe 54 in a pulse-echo operation. After receiving a flaw signal, the algorithm of the system provides automatically for measurement to be made of other key set-up parameters that include the length of water path between central transducer 54 and the front surface 60 of sample material 20, and the depth of the flaw 22 within sample material 20. These measurements are obtained by digitizing the elapsed time between the transmit pulse and the front surface reflection and flaw reflection, respectively. With this information, the required angle of incidence for the perimeter transducers 58 is computed and set by stepping motor 15. Next, TR switch 46 switches the transducers 12 to a pitch-catch mode that operates the central transducer 54 in the transmit mode and sequentially each of the six perimeter transducers 58 in a catch mode. For each one of these multiplex conditions, the total elapsed propagation time from the initiating pulse in central transducer 54 to receipt of flaw signals in the receiving perimeter transducers 58 is digitized and compared with the previously measured roundtrip pulse echo signal on central transducer 54. Adjustments are then made automatically by stepping motors 16 in the water path length for each of the perimeter transducers 58 so that the total transmit times are everywhere equal for all transmit-receive combinations. This equal timing feature has several advantages both in later data processing sequences and in the measurement of accoustic velocity differences in the media. Equalization of time paths, in the preferred embodiment, must be within 100 nanoseconds. At this point, the system is ready to receive data from transducers 12 to process the same into a reconstruction of flaw 22 (FIG. 8, reference numeral 130).

Figure 8:
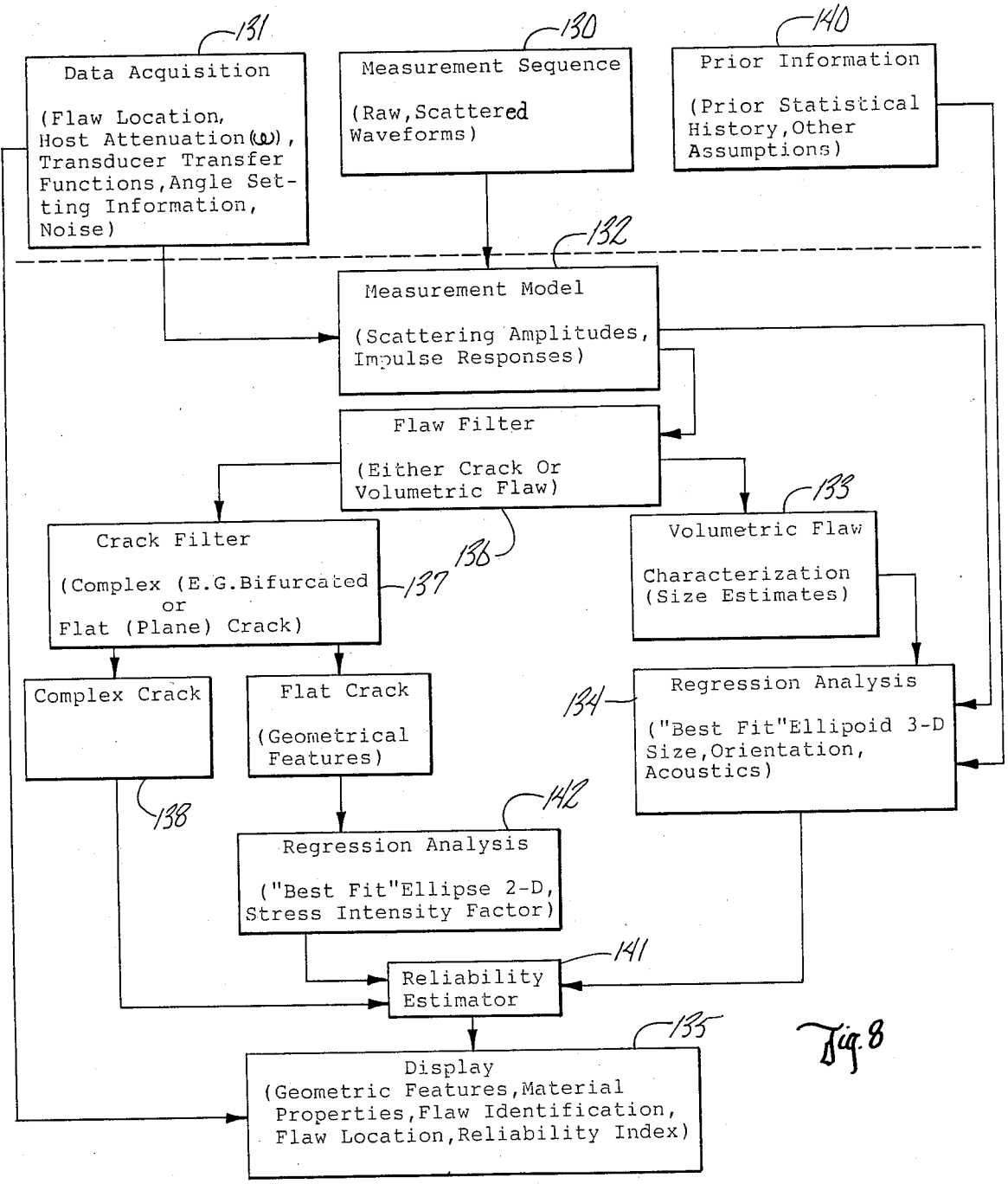
FIG. 8 is a flow diagram of the operation of the system according to the invention.

Step 3—Data Acquisition (FIG. 8, reference numeral 131). Following the initialization procedure and adjustments, the program automatically sequences transducers 12 through a combination of pulse-echo and pitch-catch combinations. Because of the number and orientation of transducers 12, nineteen different look or view angles of the flaw 22 are possible for a given angular setting. They consist of pulse-echo responses on all seven transducers 12, and nine pitch-catch responses resulting from utilization of central and peripheral transducers 54 and 58. As part of the acquisition, the wave forms are digitized by digitizer 42 and averaged, and stored in graphics computer 32.

Step 4—Corrections. Following data acquisition, certain post-processing correction of the transducer data is required. All of the remaining steps are controlled by the software and computers 32 and/or 34 according to the decision tree algorithm set forth in FIG. 8. The corrections of this step include the creation of a measurement mode (FIG. 8, reference numeral 132). The wave forms acquired in the previous step are corrected for the effects of attenuation, diffraction, and interface losses using this measurement model. Transducer 12 references are deconvolved resulting in absolute scattering amplitudes. Such steps are well known within the art.

Step 5—Inverse One Dimensional Born Approximation. The inverse Born sizing procedure, well known within the art, is used to estimate the tangent-plane-to-centroid-distance ($R_e$) for each absolute scattering amplitude. In other words, the one dimensional inverse Born approximation estimates the distance from the center of the flaw to the front surface tangent plane of the flaw (FIG. 8, reference numeral 133).

Step 6—Impulse Response Area. This step integrates the area under the inverse Fourier transformed scattering amplitudes to be used in the next step (Regression Analysis) to extract the flaw acoustic impedance.

Step 7—Regression Analysis (FIG. 8, reference numeral 134). Six geometric parameters that describe the "best fit" ellipsoid to the data are derived by regression analysis, which is well known within the art. The six geometric parameters include three semi-axes and three Euler orientation angles. The regression inputs include the radius estimates $R_{a(i)}$ and their associated angles $\alpha_i$ and $\beta_i$. In effect, the regression analysis selects a general ellipsoid to "best fit" the data. The regression analysis then proceeds to determine values for three semi-axes of the ellipsoid to determine its size and shape and three Euler angles that describe its orientation. The use of this technique was suggested as a way to approach the inverse problem in the long wave length approximation. It is quite general and permits descriptions of either cracks or inclusions and voids in host material 20.

For example, a two dimensional element is closely approximated by a determination of three semi-axes if one of the semi-axes is small compared with the other two. Results from fracture mechanics show that failure initiating microcracks nucleate selectively about inclusions of various compositions and eventually grow into cracks under flaw growth conditions. While this assumption does not focus attention on the failure initiating microcracks per se, it does permit reasonable descriptions of the inclusions (or voids) that are necessary to nucleate the micro-cracking to be obtained. The use of the front surface echo analysis, which yields values of the acoustic impedance of the scatterer, assists in this manner. This measurement permits an estimate of the identity of the scattering center to be made (e.g., void, composition of inclusion) from which it can be predicted from materials knowledge whether or not there are likely to be surrounding micro-cracks. Theoretical advances in inverse scattering or the development of a prior history that describes specific characteristics of flaws in a given materials usage or processing environments may assist in verifying the elipsoidal assumption.

Step 8—Flaw Reconstruction and Identification. After derivation of the relevant reconstruction values from the inverse Born and regression analysis operations, reconstruction of flaw 22 proceeds to approximate size, shape, and orientation of flaw 22. Utilizing the three semi-axes and three Euler angles, a three dimensional approximation is derived.

Step 9—Documentation. The software programming includes known-in-the-art procedures and methods for taking the reconstructed flaw approximation and documenting it, either visually on a conventional computer CRT screen, or in hard copy printout (FIG. 8, reference numeral 135).

The flow chart of FIG. 8 follows the general outline of the steps shown and discussed in Table 1. Additional features (not a part of the present invention) in the preferred embodiment software according to this flow chart could include the following. The ability to add in prior statistical history or other assumptions (see reference numeral 140) regarding host material 20 could assist in making the regression analysis more complete and accurate. Additionally, it will be noted that the flow diagram splits into two different routines depending on whether the perceived flaw is a crack or a volumetric flaw. If a crack, the three dimensional "best-fit" elipsoid modeling procedure could be bypassed for simply a two dimensional best fit elipse model including a stress intensity factor based upon its geometry to assist in determining its characteristics; such as its propensity to transform into a void, or to crack further (see reference numerals 136, 137, 138, 139, 140, and 142).

It can also be seen that the software programming could include reliability estimator routines (see reference numeral 141) which can perform an error analysis on the reconstruction to give an idea of how close to the actual flaw the estimation is.

Finally, the display and/or documentation of the flaw can take on many forms, and include different information, all of which is designable as is known in the art and according to choice.

Figure 9:
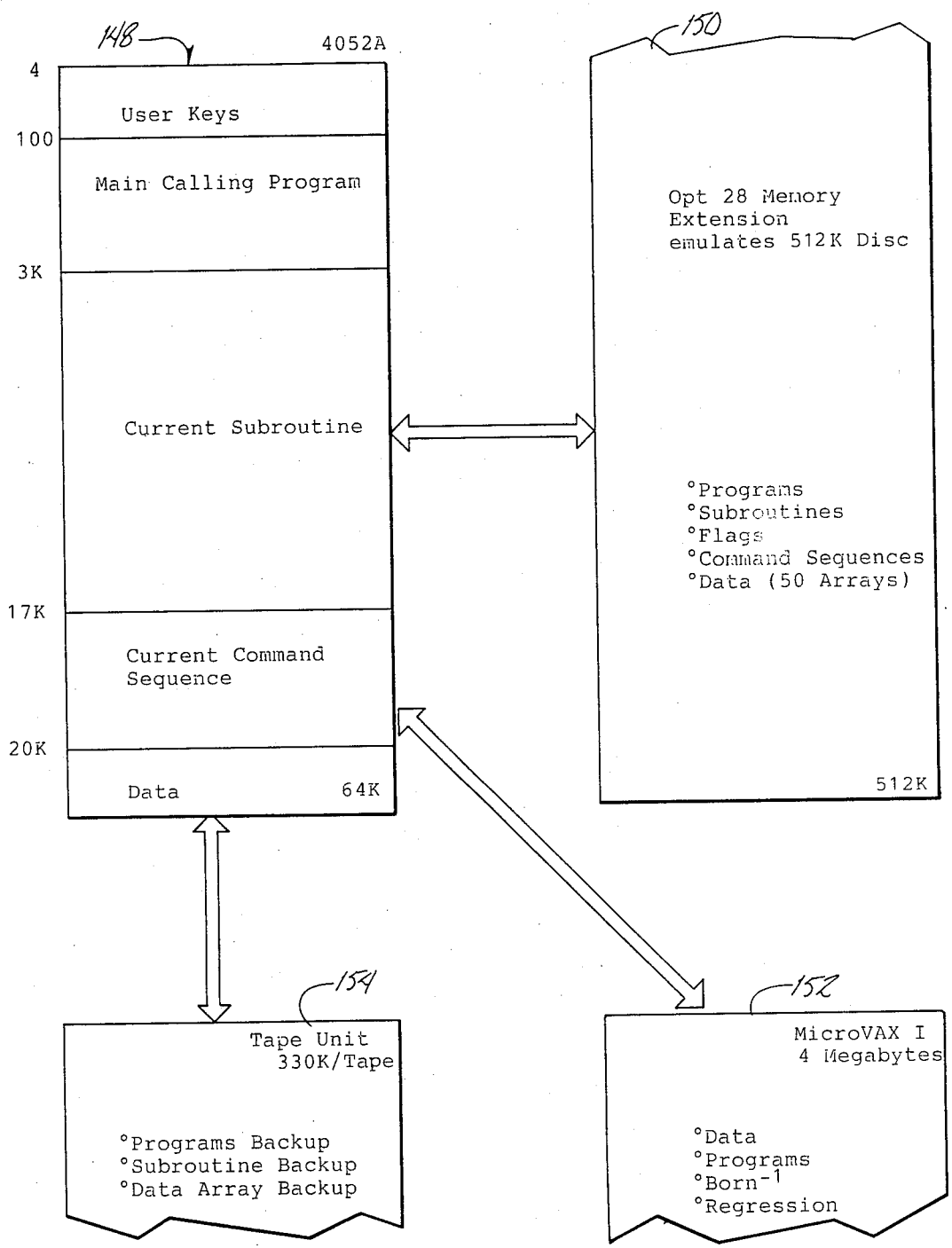
FIG. 9 is a schematic diagram of the software programming memory utilized with the invention.

FIG. 9 is a schematic of the storage space for computers 32 and 34 of the preferred embodiment of the invention and presents a schematic depiction of memory-/processing management of the system. As can be seen, the main operating memory (depicted at reference numeral 148) of the system exists with respect to graphics computer 32 being a 64K memory of which the first 96 or so lines are dedicated to storing the mnemonics for the user keys, which are reserved to hold special instructions for the dedicated keys to perform the specialized operations, for example moving transducer assembly 14 up, down, or horizontally, or switching transducers 12 from one mode to the other, etc. The next portion of this memory (up to 3K of memory) contains the main calling program for the system. This coordinates the addressing and other manipulation of software in the various other memories. 14K of memory is devoted to pulling and storing the subroutine currently in use in this main memory whereas 3K of memory stores the current command sequence. Finally, the remaining 44K of memory is reserved for data.

FIG. 9 also shows that an Optional 28 Memory Extension (reference numeral 150), which emulates a 514K disc, stores programs, subroutines, flags, command sequences, and fifty arrays of data in its 512K storage. Such a system frees the main memory of graphics computer 32 space to be utilized as discussed above.

Furthermore, the mainframe MicroVAX I computer 34 contains four megabytes of storage space (reference numeral 152) for storing data, programs, and inverse one dimensional Born and regression procedures; all of which is directly accessible to main memory of graphics computer 32.

Finally, a tape unit 154 having 330K/tape memory is utilized to provide program, subroutine, and data array backup storage.

All such memory and memory utilization is conventional as is known within the art. Memories 150, 152, and 154 are all communicable with memory 148 via conventional computer means.

An overview summary of the software and its operation and relationship to the hardware is presented later in this application. Also, exact documentation and instructions for the one dimensional inverse Born algorithm according to the present invention are set forth later.

The general operation of electronic assembly 18 is as follows as again depicted in FIG. 1. The principal ultrasonic signal path of the system consists of the generation of an electronic voltage pulse in Panametrics pulser/receiver 44 and transmittal of the initating pulse to the selected transducer 12 through a Textronix M15010 switch 46 which is under control of graphics computer 32 that controls transducer 12 selection and sequencing. The detected signal is transmitted back to the Panametrics pulser/receiver 44 through a Comlinear preamplifier 48 of 20 dB gain that is protected from the initiating pulse by appropriate diode buffers (not shown) and through the Textronix switch 46. Each transducer 12 of the assembly is coupled to a preamplifier 48. Detected wave forms are then transmitted to Textronix 7912AD converter (digitizer 42) where they are digitized, averaged, and stored in graphics computer 32. Detailed calculations are then performed in the MicroVAX I computer 34 as they are needed. The graphics computer 32 also serves as the control center to program and execute the inspection cycle. This portion of the cycle is done through IEEE bus 36 to the Textronix switch 46 and to the stepping motor drive 40 which controls the angle of incidence (via stepping motor 15) and transducer propagation path link (via stepping motors 16). It is initiated through a software program (see FIGS. 8 and 9) for data acquisition previously described.

A specific example of the functioning of the invention 10 is set forth as follows. FIG. 10 shows a stainless steel particle 160 (acting as a flaw) with an approximate shape of a prolate spheroid embedded in a Lucite host material 162. The spheroid flaw 160 was pre-formed with the known parameters of semi-axes of 47 and 96 micrometers tilted about 7 degrees from the parallel faces of sample material 162.

FIG. 11 shows a polar plot of inversion results obtained at a variety of viewing angles, such as previously described. $\alpha'$ is the polar angle and $\beta'$ is the azimuthal angle in the solid host material 162. The numbers given in the plot are values in micrometers of the tangent plane distances obtained from the inverse Born solution.

FIG. 11 is a conventional polar plot where each plotted point has an $\alpha$ and $\beta$ coordinate (standard spherical coordinates). Each plotted dot is a data point, and the number beside it is the measured size, in microns, of a perspective radius estimate of flaw 160 (FIG. 10). In FIG. 11, flaw or detect 160 is depicted in the center of the polar plot.

FIG. 12 shows the tangent plane distances of the equivalent ellipsoid obtained by the least square's iteration for both the x'z' and y'z' cross-section of the ellipsoid. Experimental points are also shown on the locus of tangent plane distances as circles 164. The experimental aperture (depicted by dashed lines 166) is also readily apparent in this Figure. The solid curve 168 in FIG. 13 shows the final reconstruction of the best fit ellipsoid to the data. The small circles 164 shown are experimental points.

A summary of the various flaw characterization parameters and Euler angles obtained for the above example are given in the following table.

TABLE 2

Results of the Elipsoidal Reconstruction For The 47 × 96 Micrometer (Semi-Axes) Inclusion

| Actual Parameters | | Ellipsoid Reconstruction | | | |
|---|---|---|---|---|---|
| | | A | B | C | D |
| $a_x$ | 47 μm | 40 μm | 27 μm | 28 μm | 0 μm |
| $a_y$ | 96 μm | 141 μm | 119 μm | 123 μm | 122 μm |
| $a_z$ | 47 μm | 50 μm | 54 μm | 53 μm | 56 μm |
| $\theta$ | 7° | 14° | 8° | 9° | 2° |
| $\phi$ | 0° | −71° | −48° | −47° | 7° |
| $\psi$ | 0° | 69° | 47° | 46° | 8° |

The final steps in the process are depicted at FIGS. 14–18. In the example shown in these Figures (different from the example of FIGS. 11–14), flaw 22 has been characterized by "best-fit" to a general elipsoid as shown by the specifications in Table 3 for the semi-axes and Eulers angles.

TABLE 3

| 3-D Perspective: 80°, 10° | |
|---|---|
| Semi-Axes in | Euler's Angles in deg. |
| C1(Ax) 394.754 | C4(Theta) 5.796 |
| C2(Ay) 424.043 | C5(Phi) −30.05999 |

TABLE 3-continued

| 3-D Perspective: 80°, 10° | |
|---|---|
| Semi-Axes in | Euler's Angles in deg. |
| C3(Az) 153.2332 | C6(Psi) 112.3558 |

Flaw impedance = 0.002

Figure 14:
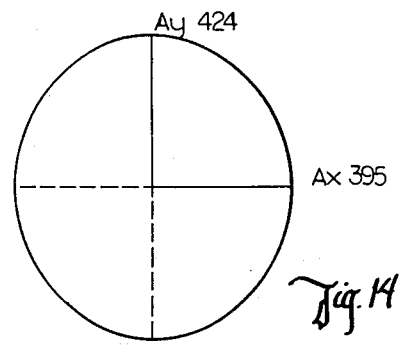
Figure 15:
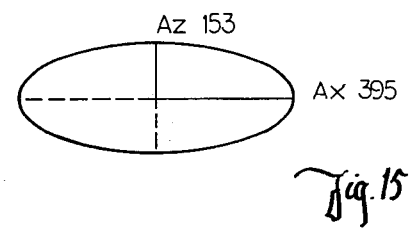
Figure 16:
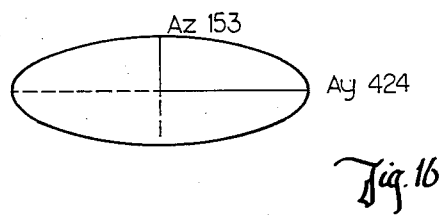
Figure 17:
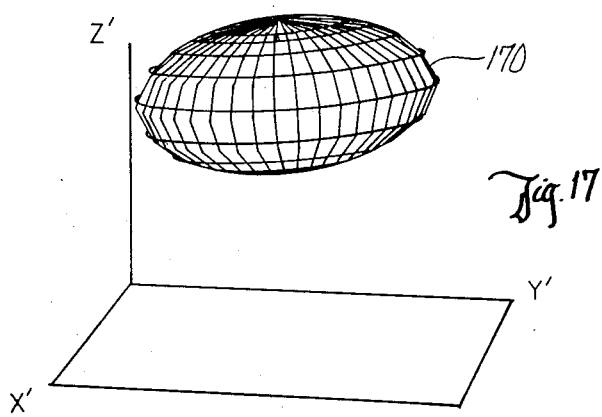
Figure 18:
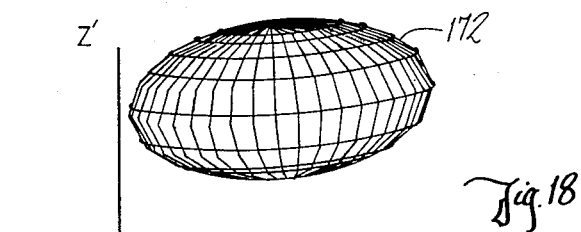

As can be seen, FIGS. 14–16 reflect the x, y, and z cross sections of the ellipsoid models 170 and 172. FIGS. 17 and 18 show the reconstructed three dimensional elipsoid approximating the flaw 22 in the host material 20 for this example.

The software of the invention is appended with this specification as a Microfiche Appendix. A brief summary of the operation of its inverse Born algorithm is contained below, and a broader overview of the entire software functioning with the apparatus of the invention follows.

DOCUMENTATION AND INSTRUCTIONS FOR THE ONE DIMENSIONAL INVERSE BORN ALGORITHM

THE SUBSEQUENT LISTINGS CONTAIN THE ASSOCIATED SOFTWARE WHICH IMPLEMENT THE ONE-DIMENSIONAL INVERSE BORN ALGORITHM AS USED IN PRACTICE AT THE AMES LABORATORY. THIS CHARACTERIZATION PROCESS IS APPLICABLE TO SIZING VOLUMETRIC FLAWS IN THE BULK OF AN ELASTIC MEDIUM.

THE MAIN PROGRAM, OR DRIVER, FOR THIS SOFTWARE, IS A MENU-DRIVEN ROUTINE WHICH ALLOWS USER CONTROL OF THE INDIVIDUAL STEPS IN THE APPLICATION OF THE INVERSE BORN APPROXIMATION. THE MENU ITEMS ARE AS FOLLOWS:

(1) . . . GET INPUT DATA
(2) . . . RE-INITIALIZE THE DATA
(3) . . . COARSE TIME SHIFT ADJUSTMENT
(4) . . . CONVOLVE DATA WITH A HANNING WINDOW
(5) . . . EXTRAPOLATE/TRUNCATE LOW END OF SPECTRUM
(6) . . . ZERO-OF-TIME CALCULATION
(7) . . . COMPUTE CHARACTERISTIC FUNCTION
(8) . . . PLOT DATA
(9) . . . STORE DATA
(10) . . . END.

EACH OF THESE STEPS WILL NOW BE ADDRESSED IN DETAIL.

ITEM 1.

THE INPUT ROUTINE PROMPTS THE USER FOR THE HOST MEDIUM ACCOUSTIC VELOCITY, FREQUENCY INCREMENT AND NUMBER OF SPECTRAL COMPONENTS IN THE SCATTERING AMPLITUDE, THE FILE CONTAINING THE FLAW SCATTERING AMPLITUDE (OR FLAW SIGNAL DECONVOLVED BY A REFERENCE WAVEFORM), AND THE MINI-

MUM AND MAXIMUM FREQUENCIES IN THE BANDWIDTH OF THE EXPERIMENTAL DATA UNDER CONSIDERATION. THE SCATTERING AMPLITUDE IS PLACED INTO AN ARRAY CALLED 'ARAW' WHICH PADS THE DATA WITH ZEROES AS DESCRIBED IN THE LISTING OF THE SUBROUTINE CALLED 'INPUT'. THIS ARRAY IS ALSO PLACED INTO AN ARRAY CALLED 'AWORK' UPON WHICH SUBSEQUENT CALCULATIONS ARE PERFORMED.

ITEM 2.

THIS ROUTINE RESTORES THE ARRAY 'ARAW' INTO THE WORK ARRAY 'AWORK' AND RESETS THE TIME SHIFT TO ZERO.

ITEM 3.

THIS ROUTINE WILL ELIMINATE SOME EXCESS PHASE FROM THE INPUT SCATTERING AMPLITUDE. FOR EXAMPLE, A SAMPLE RUN OF THE SOFTWARE SHOWS THE RAW SCATTERING AMPLITUDE AS INPUT. THE PHASE AND OSCILLATORY NATURE OF THE REAL AND IMAGINARY PARTS OF THE SCATTERING AMPLITUDE WOULD BE RAMP-LIKE IN APPEARANCE. THIS ARISES DUE TO EXCESS PHASE CAUSED BY AN INCORECT ORIGIN OF TIME. THIS ROUTINE ROUGHLY ADJUSTS THE PHASE OF THE SCATTERING AMPLITUDE BY SUBTRACTING A LINEAR PHASE CORRECTION OF THE FORM 1*2*PI*F*t WHERE THE TIME t IS COMPUTED AS AN AVERAGE VALUE OVER THE FREQUENCIES IN THE BANDWIDTH. THIS WILL NOT, IN GENERAL, CORRECT THE SCATTERING AMPLITUDE FOR THE ZERO-OF-TIME ADJUSTMENT, BUT WILL TYPICALLY ELIMINATE MUCH OF THE OSCILLATION IN THE REAL AND IMAGINARY PARTS OF THE SCATTERING AMPLITUDE. THE SAMPLE RUN SHOWS THE RESULTS OF THIS CORRECTION. THIS ROUTINE IS AUTOMATIC WITH NO USER INPUT. ALSO NOTE THAT THIS SHIFT IS PERFORMED ON THE RAW DATA FILE, 'ARAW', SO THAT A HANNING WINDOW OR TRUNCATION/EXTRAPOLATION MUST BE REDONE AFTER THE COARSE TIME SHIFT.

ITEM 4.

THIS ROUTINE MULTIPLIES THE SCATTERING AMPLITUDE BY A COSINE-SQUARED (HANNING) WINDOW CENTERED AT ZERO FREQUENCY. THE EFFECT OF THIS IS TO SMOOTH THE HIGH FREQUENCY END OF THE SCATTERING AMPLITUDE SPECTRUM TO ZERO AMPLITUDE. (THIS SMOOTHING IS A FEATURE USED ROUTINELY AND IS A RECOMMENDED PRACTICE.) IF THIS WINDOW IS USED, IT IS RECOMMENDED THE THE HIGH FREQUENCY LIMIT OF THE SCATTERING AMPLITUDE, WHICH IS ENTERED IN ITEM 1 ABOVE, BE SET TO APPROXIMATELY 25% HIGHER THAN THE ACTUAL HIGH FREQUENCY LIMIT OF THE EXPERIMENTAL DATA IN ORDER TO MINIMIZE ADVERSELY AFFECTING THE HIGH FREQUENCY CONTENT OF THE DATA.

ITEM 5.

THIS ROUTINE WILL ALLOW EITHER TRUNCATION OR SMOOTHING OF THE LOW FREQUENCY END OF THE SCATTERING AMPLITUDE SPECTRUM. IF TRUNCATION IS CHOSEN, SPECTRAL COMPONENTS OF THE SCATTERING AMPLITUDE BELOW THE LOW FREQUENCY LIMIT OF THE BANDWIDTH ARE SIMPLY SET TO ZERO. IF EXTRAPOLATION IS CHOSEN, THE DATA WILL BE FIT TO A POLYNOMIAL REPRESENTATION AT LOW FREQUENCY AND THE DATA WILL BE EXTRAPOLATED TO ZERO FREQUENCY BY THESE POLYNOMIALS. THE FORM OF THE POLYNOMIALS AND THE MEANS OF FITTING TO THE DATA ARE DISCUSSED IN THE NOTES MENTIONED IN THE FIRST PARAGRAPH AND IN THE LISTING FOR SUBROUTINE 'EXTRAP'. IN THIS ROUTINE, THE USER IS PROMPTED FOR A SINGLE NUMBER, A VALUE OF ZERO INDICATING TRUNCATION AND A NONZERO VALUE INDICATING THE NUMBER OF TERMS TO BE RETAINED IN THE EXTRAPOLATING POLYNOMIALS.

ITEM 6.

THIS ROUTINE CALCULATES THE ZERO-OF-TIME ESSENTIAL FOR IMPLEMENTATION OF THE INVERSE BORN APPROXIMATION. USE OF THE INVERSE BORN APPROXIMATION REQUIRES A PHASE REFERENCE WHICH COINCIDES WITH THE LOCUS IN SPACE CORRESPONDING TO THE CENTER OF THE FLAW ASSUMING THE FLAW IS NOT PRESENT (OWING TO THE WEAK SCATTERING ASSUMPTION IMPLICIT IN THE DERIVATION OF THIS ALGORITHM). THE TECHNIQUE OF THIS CALCULATION IS TO COMPUTE THE 'AREA FUNCTION' AND ITS DERIVATIVE (SEE EXPLANATORY NOTES) AND THE IMPULSE RESONSE OF THE FLAW (INVERSE FOURIER TRANSFORM OF THE SCATTERING AMPLITUDE). THESE THREE ARRAYS ARE DISPLAYED SIMULTANEOUSLY IN ORDER TO IDENTIFY THE FEATURES OF INTEREST AS FOLLOWS: IN THE DISPLAY OF THE IMPULSE RESPONSE, ONE MUST LOCATE THE SIGNAL FEATURE CORRESPONDING TO THE FRONT SURFACE REFLECTION FROM THE FLAW (I.E., THE FIRST PEAK). THEN THE PEAK IN THE AREA FUNCTION WHICH OCCURS JUST AFTER THE PEAK IN THE IMPULSE RESPONSE AND WHICH HAS THE OPPOSITE POLARITY OF THE FRONT SURFACE PEAK OF THE IMPULSE RESPONSE

IS IDENTIFIED. THE TIME OF OCCURENCE OF THIS PEAK IS THE TIME CORRECTION WHICH IDENTIFIES THE CORRECT ZERO-OF-TIME. THE DERIVATIVE OF THE AREA FUNCTION IS ALSO DISPLAYED SINCE A PEAK IN THE AREA FUNCTION WILL CORRESPOND TO A ZERO-CROSSING IN ITS DERIVATIVE. THIS MAY BE EASIER TO LOCATE THAN A PEAK IN THE AREA FUNCTION. ONCE THE CORRECT PEAK (OR ZERO CROSSING) IS LOCATED, THE USER IS PROMPTED FOR THE DESIRED TIME SHIFT TO APPLY TO THE SCATTERING AMPLITUDE. THIS TIME IS ACCORDING TO THE CONVENTION THAT POSITIVE TIME WILL SHIFT THE AREA FUNCTION PEAK TO THE RIGHT AND NEGATIVE TIME WILL SHIFT TO THE LEFT.

THE TIME SHIFT IS PERFORMED UPON THE RAW SCATTERING AMPLITUDE DATA, SO THE USER MUST RE-DO A HANNING WINDOW OR EXTRAPOLATION AFTER SHIFTING. THE USER IS PROMPTED FOR THESE RECALCULATIONS AFTER THE TIME SHIFT IS CALCULATED. THE ABOVE CALCULATIONS ARE REPEATED (I.E. THE AREA FUNCTION, ETC. ARE COMPUTED AND DISPLAYED AND THE USER IS PROMPTED FOR A TIME CORRECTION) SO THAT THE USER MAY 'FINE-TUNE' THE TIME SHIFT REPEATEDLY UNTIL A ZERO VALUE IS ENTERED FOR THE TIME SHIFT. AFTER THIS STEP, THE CONTENTS OF 'AWORK' IS THE SCATTERING AMPLITUDE OF THE FLAW, APPROPRIATELY SMOOTHED, WITH THE CORRECT PHASE REFERENCE FOR THE INVERSE BORN APPROXIMATION. AN ADDITIONAL ROUTINE HAS BEEN ADDED TO FACILITATE THE ZERO-OF-TIME DETERMINATION. THIS ROUTINE LOCATES THE FIRST ZERO CROSSINGS OF DAREA JUST TO THE LEFT AND JUST TO THE RIGHT OF THE TIME ORIGIN AND PROMPTS THE USER TO ACCEPT ONE OR NEITHER OF THESE TIMES FOR THE NEXT TIME SHIFT. IF ONE OF THESE TIMES IS SELECTED, THE APPROPRIATE TIME SHIFT IS PERFORMED AUTOMATICALLY. IF NEITHER IS SELECTED, THE USER IS PROMPTED FOR A TIME SHIFT INCREMENT AS DESCRIBED ABOVE.

ITEM 7.

THIS STEP PERFORMS THE ACTUAL INVERSE BORN ALGORITHM. THE RESULT OF THIS STEP IS THE CHARACTERISTIC FUNCTION OF THE FLAW, WHICH IS DEFINED, IN PRINCIPLE, TO BE UNITY WITHIN THE FLAW AND ZERO OUTSIDE. IN PRACTICE, DUE TO FINITE BANDWIDTH CONSTRAINTS, THE CHARACTERISTIC FUNCTION DOES NOT HAVE A SHARP DROP-OFF AT THE FLAW RADIUS, BUT HAS A GRADUAL TRANSITION FROM UNITY TO ZERO AND TYPICALLY EXHIBITS SOME RINGING AS WELL. TWO METHODS ARE USED TO ESTIMATE THE FLAW RADIUS. FIRST, AN ESTIMATE IS OBTAINED AS THE RADIAL POSITION OF THE CROSSING OF THE 50% CONTOUR OF THE CHARACTERISTIC FUNCTION (OR THE ONE AT THE HIGHEST RADIAL POSITION IF SEVERAL OCCUR). ALTERNATIVELY, AN ESTIMATE OF THE FLAW RADIUS IS OBTAINED AS THE AREA UNDER THE CHARACTERISTIC FUNCTION DIVIDED BY ITS PEAK VALUES.

ITEM 8.

THIS SUBROUTINE, WHICH MUST BE IMPLEMENTED ACCORDING TO THE USER'S SYSTEM, SIMULTANEOUSLY DISPLAYS THE MAGNITUDE AND PHASE AND THE REAL AND IMAGINARY PARTS OF THE CURRENT WORK ARRAY, CALLED 'AWORK' IN THE SOFTWARE. THE COMMON BLOCK DENOTED '/WORK/' MUST BE INCLUDED IN THIS ROUTINE.

ITEM 9.

THIS ITEM ALLOWS STORAGE OF THE VARIOUS ARRAYS OFF-LINE FOR LATER USE, E.G. PLOTTING, ETC.

ITEM 10.

THIS TERMINATES EXECUTION OF THE PROGRAM.

NOTE: FOUR ROUTINES ARE USED IN THE ACCOMPANYING SOFTWARE FOR PLOTTING PURPOSES AND MUST BE SUPPLIED BY THE USER. THESE ARE "PLOT", "PLOT3", "PLOTC", AND "CLSCRN". THE PURPOSE OF EACH ROUTINE IS:

PLOT --- SEE ITEM b 8. ABOVE.
PLOT3 --- USED TO SIMULTANEOUSLY DISPLAY THE AREA, DERIVATIVE OF THE AREA FUNCTION, AND THE IMPULSE RESPONSE.
PLOTC --- USED TO DISPLAY THE CHARACTERISTIC FUNCTION
CLSCRN --- USED TO REFRESH THE SCREEN (MY TERMINAL HAS A STORAGE-TYPE CRT DISPLAY)

To further assist in describing the invention, the following is a narrative description of the entire multi-viewing transducer data acquisition and signal processing software, its interface to the hardware of the invention, and references to the research papers upon which certain of the procedures are based.

In the nondestructive evaluation of material defects, size, shape, and orientation are important flaw parameters in structural integrity assessment. The apparatus and the signal processing algorithms of the present invention were specifically designed to make use of the theoretical developments in elastic wave inverse scattering in the long and intermediate wavelength regime, resulting in an ellipsoidal model which most closely approximates the actual flaw.

As an overview of the implementation of the theoretical work, pertinent references should be cited and are incorporated by reference. A numbered listing of references is set forth later. In this description the reference works will be referred to by list number (in parentheses) and sometimes by author. The software programming referred to for this invention is attached as a Microfiche Appendix to this specification. Kohn and Rice (2) show that long wavelength elastic scattering data from an arbitrary localized defect in a uniform isotropic medium has a maximum information content of 22 parameters which are characteristic of the defect. Six of those parameters determine size, shape, and orientation of the ellipsoid approximating the flaw and a seventh parameter represents the flaw's acoustic impedance.

FIG. 1 is a schematic representation of the hardware and how it is interfaced. Graphics computer 32, a Tektronix 4052A, is the controlling computer and communicates with the other instrumentation via IEEE 488 interface bus (called GPIB—General Purpose Interface Bus) [identified in FIG. 1 by reference numeral 36]. The Digital Equipment Corporation (DEC) Microvax computer 34 serves as a "number cruncher" and mass storage device to reduce overall processing time by as much as an order of magnitude.

FIG. 9 shows the multiviewing transducer data acquisition system memory/processing management. Because the on-line memory of the Tektronix 4052A (graphics computer 32) is only 64K bytes, all of the software it utilizes resides in an extended memory in the form of subroutines and command sequences. Subroutines are pieces of software that perform specific tasks, whereas command sequences are sequential combinations of individual subroutines to accomplish a much more comprehensive task. As an example, "M3.SEQ" is a command sequence made up of all the subroutine calls necessary to acquire a set of 19 waveforms for a given reconstruction measurement.

A controlling program "MON.PROG" resides within the 64K bytes of memory, sequentially pulling in the appropriate command sequences and subroutines for the task at hand. There are approximately 200 pieces of software to accomplish all the functions. About one fourth of those provide a convenient computing environment for analysis, data management, processing, displays, etc. as well as general housekeeping chores to keep track of every thing in an orderly manner. Some subroutine examples are:

| | |
|---|---|
| "DAT" | Display date from VAX/VSM |
| "DEC" | Deconvolve two arrays, Q=10% of MAX |
| "DEC 0" | Deconvolve two arrays, set Q=0 |
| "DF" | Determine depth of flaw |
| "DF ?" | Show recorded depth of flaw |
| "DF 1.27" | Set depth of flaw to 1.27 cm |
| "DIG" | Digitize. Ave=Flag(38), Sub BKG= Flag (42) |
| "DIG 5E-7" | Digitize, Pad to .5us/div if appropriate |
| "DIR" | Directory of all opt28 memory files |
| "DIR 6" | List tape directory No. 6 |
| "DIR *.SEQ" | Directory of files ending with "SEQ" |
| "DIS" | Display current waveform |
| "DH" | Determine depth of host (thickness) |
| "DH ?" | Show recorded depth of host |
| "DH 2.54" | Set depth of host to 2.54 cm |
| "DH 8.1300" | Step motor No. 8 "down" 1300 steps |
| "DW" | Determine depth of water (waterpath) |
| "DW /" | Show recorded depth of water |
| "DW 6.07" | Set depth of water to 6.07 cm |

The software to perform flaw reconstruction can be operated from the controlling computer manually, or may be menu driven. Table 1, previously discussed, shows the basic menu. The user may select any menu item independently, or select a starting point with all processing steps being automatic to the end of the menu. Table 1 also serves as a useful outline of the major processing steps to accomplish flaw reconstruction and will be followed in the discussion below.

Edit Experiment Parameters

The details of volumetric flaw characterization currently in place include the following elements:

1. Data Acquisition—Backscatter waveforms from a target flaw are digitized for nineteen independent pulse-echo, pitch-catch measurements.

2. Measurement Model—The waveforms are corrected for the effects of attenuation, diffraction, and interface loses using the measurement model. Transducer references are deconvolved resulting in absolute scattering amplitudes.

3. Inverse Born approximation—The inverse Born sizing procedure is used to estimate the tangent plane to centroid distance ($R_e$) for each absolute scattering amplitude.

4. Regression Analysis—Six geometric parameters (three semi-axes and three Euler orientation angles) that describe the "best fit" ellipsoid to the data are derived by regression analysis. The regression inputs include the radius estimates $R_e(i)$ and their associated angles $\alpha_i$ and $\beta_i$.

These elements require knowledge of specific parameters associated with the conditions under which each waveform was acquired. Each waveform is originally digitized with 9 bytes (512 points or levels) resolution both vertically (amplitude) and horizontally (time). Each acquired waveform has a file name and is stored with the following convention:

A$\phi$,A(512),A1,A2(23) stored as "FILNAM.EXT"

A$\phi$ is an integer representing the number of horizontal points in array "A".

A is the data array (usually 512 floating point numbers).

A1 is a horizontal scale factor, indicating the time window of the digitizing instrument.

A2 is an array of 23 parameters corresponding to the measurement conditions applicable to the waveform.

The file name (FLAW11.T46, for example) also conveys necessary information.

"FLAW" indicates that the waveform is an original back-scatter signal reflected from the flaw.

"11" indicates that this is the eleventh waveform acquired in a predetermined data acquisition pattern.

".T46" identifies this as a particular measurement.

Below is shown a display of the 23 experimental and material parameters associated with file "FLAW11.T46".

| EXPERIMENT PARAMETERS - FLAW11.T46 | | | |
|---|---|---|---|
| 1. TRANSDUCER (T) | A2(1) | 1 | SERIAL No. 0 |
| 2. TRANSDUCER (R) | A2(2) | 5 | SERIAL No. 0 |
| 3. POLAR (T) | A2(3) | 0 | SOLID 0 deg. |
| 4. POLAR (R) | A2(4) | 11.7 | SOLID 27.3369 deg. |
| 5. AZIMUTHAL (T) | A2(5) | 0 | deg. |
| 6. AZIMUTHAL (R) | A2(6) | 180 | deg. |
| 7. POSITION (T) | A2(7) | 2.54 | cm |
| 8. POSITION (R) | A2(8) | 2.54 | cm |
| 9. EFF RADIUS (T) | A2(9) | 0.3005 | cm |
| 10. EFF RADIUS (R) | A2(10) | 0.3005 | cm |
| 11. Dw (T) | A2(11) | 2.76 | cm |
| 12. Dw (R) | A2(12) | 2.838 | cm |
| 13. Df (T) | A2(13) | 0.918 | cm |
| 14. Df (R) | A2(14) | 1.5876 | cm |
| 15. PULSER ATTEN | A2(15) | 10 | dB |
| 16. Fmin | A2(16) | 2 | MHz |
| 17. VELOCITY (L) | A2(17) | 0.5968 | cm/us |
| 18. VELOCITY (S) | A2(18) | 0.3764 | cm/us |
| 19. DENSITY | A2(19) | 2.2 | gr/cm |
| 20. ATTENUATION Ao | A2(20) | 1 | |
| 21. ATTENUATION n | A2(21) | 1 | |
| 22. Re (Experiment) | A2(22) | 115 | microns |
| 23. Re (Theory) | A2(23) | 115 | microns |

Figure 19:
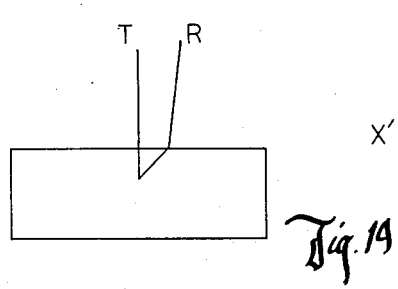
FIGS. 19–23 are illustrations and visualizations similar to FIGS. 11–18 depicting the processes, operations, and results of the system and method according to the invention.

FIG. 19 should be referred to with regard to the preceding experiment parameters, as the parameter T corresponds to central transducer 54 and parameter R corresponds to a perimeter transducer 58 as illustrated in FIG. 19. The subroutine "M1.SUB" is used to generate this display allowing the user to view and modify any of the data. Most of the information is automatically inserted by the running programs, however, some essential information, such as acoustic velocity and density of the host material not determined in the measurement process, must be entered by the user in the beginning.

Setup and Alignment

Once a target flaw 22 has been found (which can be determined by systematically scanning a part for a defect with a program such as "C.SUB") steps are taken to select appropriate distances and angles to focus the sparse array of transducers such that their ultrasonic beams intersect the target flaw with equal acoustic paths. Subroutines "M2.SEQ" and "SA.SUB" with user interaction determine all the geometries, set the perimeter transducer angles, and equalize time paths by adjusting perimeter transducers up and down along their own axes. The geometry and the associated equation are shown and discussed with regard to FIG. 7.

It is often insufficient to simply select No. 2 (setup and alignment) from the menu and then proceed on. Sometimes there are trade-offs to be made between aperture (the angles of the perimeter transducers), depth of water, and signal-to-noise ratio. Such decisions are made by the operator in an interactive mode. Appropriate references are (4), (5), (6), (7), (8), and (9) (see listing of References).

Data Acquisition

Data acquisition is performed by "M3.SEQ" which selects the appropriate transducers and digitizes time domain waveforms. FIG. 2 depicts the seven transducers employed. Nineteen combinations of pitch-catch and pulse-echo signals are used, representing fairly uniform spacial sampling of the solid angle aperture defined by the perimeter transducer angle.

Filtering the flaw data reduces the effects of noise in subsequent processing, which is often necessary for reliable reconstruction results. The filtering subroutines are: "FIL.SEQ", "WIN.SUB" and "GAT.SUB".

Thompson-Gray Measurement Model

The acquired backscatter signal from a target flaw is a convolution of the transmitting transducer characteristics, the flaw being "illuminated" with ultrasound, and the receiving transducer characteristics. Furthermore, the sound beams also suffer losses due to diffraction, reflection and attenuation. The Thompson-Gray measurement model accounts for all of these factors resulting in an absolute scattering amplitude which is characteristic solely of the target flaw (See reference paper (5), listing of References).

The measurement model requires a reference waveform generated in a separate measurement which is entirely independent of the measurement geometry or the material properties. A front surface echo is taken from a reference material and corrected for reflection coefficients and diffraction to produce a reference waveform "REFi.NEW" denoted as " " in the equations of reference (5). The program which generates these references is "M22.SEQ". The actual corrections are made in "ADJ.SUB".

Appropriate references are (5), (9), (10), (11), (12).

1-D Inverse Born Approximation

Details of the 1-D inverse Born approximation software appear at the previous section entitled "Documentation and Instructions for the One Dimensional Inverse Born Algorithm". The relevant work appears in references (13), (14), (15), (16), (17), (18), (19), (20).

The 1-D Born gives a tangent-plane-to-centroid "radius estimate" of the flaw for each of the scattering amplitudes corresponding to the active transducer (pulse-echo) or transducers (pitch-catch).

This software "BORNA.FOR" and associated subroutines "BORNSUBA.FOR" are written in FORTRAN and run on Microvax computer 34 to reduce overall processing time. "M5.SEQ" transfers the data and starts the FORTRAN programs.

Inpulse Response Area Function

"M6.SEQ" which makes use of "ARE.SUB" calculates the area under the peak of each impulse response (the time domain Fourier transform of the scattering amplitude). This number is later used to determine the acoustic impedance of the flaw. Appropriate references are (2) and (11).

Regression Analysis

The 1-D inverse Born approximation gives a set of tangent-plane-to-centroid "radius" estimates for each of the perspectives in the measurement. The tangent-plane-to-centroid distance is transformed into tangent-point-to-center-radius estimate. Parameters of size, shape, and orientation of a general ellipsoid most closely approximating the actual flaw are determined by regression analysis. This regression analysis including the above transformation is accomplished by "NREG7C.FOR" with "MINA.FOR" performing the regression analysis function in FORTRAN on Microvax computer 34.

Of the 22 parameters characteristic of the flaw noted by Kohn and Rice (2), three of these represent the three semiaxes of the resultant ellipsoid, three are Euler angles of rotation describing the ellipsoid orientation, and one parameter is the acoustic impedance of the flaw. Appropriate references are (3), (4), (5), (7), (8), (11).

"M7.SUB" is used to run the regression FORTRAN programs on the Microvax 34. "NREG7WF.FOR" is a version of the regression analysis that incorporates weighting factors for the various radius estimate based on perspective and flaw orientation determined in a previous iteration.

Display of Regression Results

"M8.SEQ" is a command sequence which displays the results both in tabular form, as well as drawing 2-D projections of the resultant ellipsoid (see Tables 6, 7 below, and FIGS. 20, 21 in association with FIGS. 14–16 and FIGS. 22 and 23). Information is displayed that allows the operator to assess and interpret the reliability of the reconstruction measurement. See references (3), (4), and (8).

Figure 20:
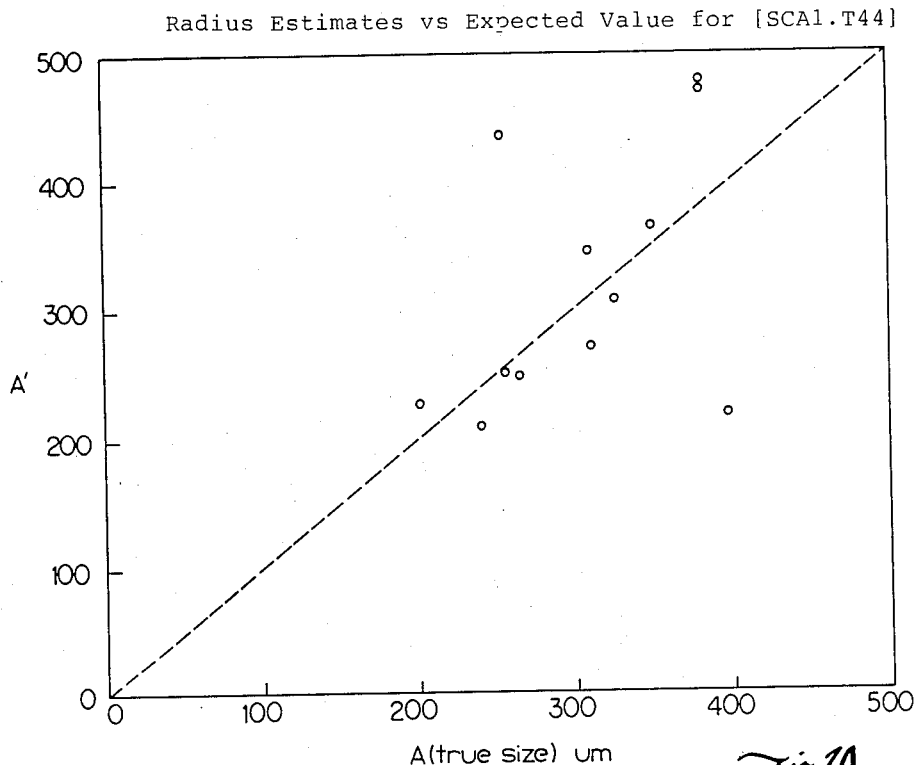

FIG. 20 plots experimentally obtained data (shown with small circles or dots) versus theoretical value (dashed line). If the experimental data (radius estimates from inverse Born calculations) were equal to theoretically predicted values, then the dots would fall along the dashed line. The bigger the flaw, the higher up along the dashed line the plotted lines will fall. FIG. 20 therefore is a correlation plot between experimentally obtained data and theoretical predicted results.

Figure 21:
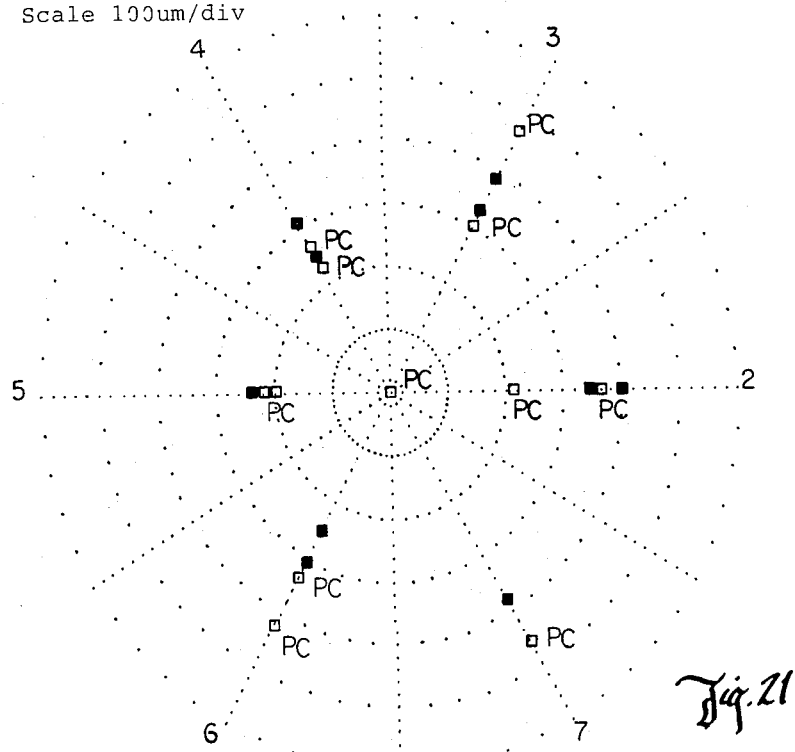

FIG. 21 is a computer drawn version of FIG. 11. The scales are different. The circular axis equals $\alpha'$ or the asmuthal angle, but instead of the polar angle, the plotted squares spaced from the center are radius estimates in microns. FIG. 21 gives a size representation of the flaw, including an estimation of its shape, e.g., circular or elliptical.

Figure 22:
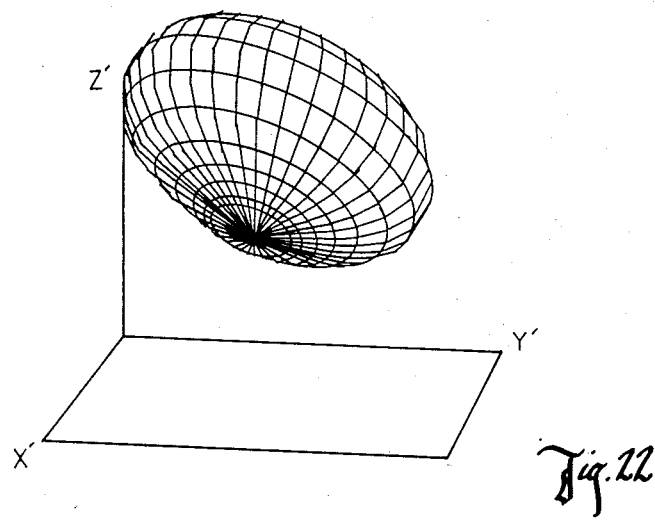
Figure 23:
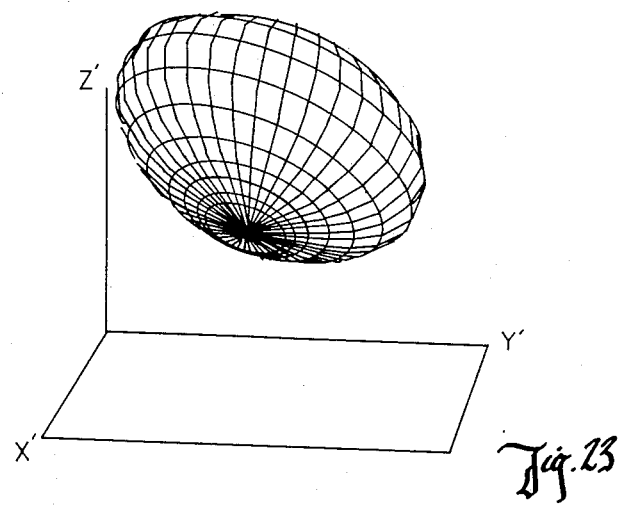

FIGS. 22 and 23 are three-dimensional plots of the radius information set forth in prior figures. FIGS. 22 and 23 represent a stereo pair of plots; FIG. 22 being the right eye version, and FIG. 23 being the left eye version. If FIGS. 22 and 23 are viewable by a stereoscope, or some other similar apparatus or method, the viewer would be able to perceive the reconstructed estimated flaw in three-dimensional vision.

TABLE 6

TABULAR RESULTS FOR SCA1.T44  Q = 10%  NO ATTN  WINZ  3, 9
Experiment   C1,...,C6   400, 380, 194, −36, 73, 28
THEORY       C1,...,C6   400, 400, 200, 0, 0, 0

| No | TR | TA(W) | RA(W) | Polar | Azmuth | Re | Theory/Tau | % Re | Area |
|----|----|-------|-------|-------|--------|-----|------------|------|------|
| 1  | 11 | 0.00  | 0.00  | 0.00  | 0.00   | 242.1 | 264.575100 | −8.51 | 0.000000 |
| 2  | 22 | 10.65 | 10.65 | 52.18 | 0.00   | 211.7 | 297.213400 | −46.71 | 0.000000 |
| 3  | 33 | 10.65 | 10.65 | 52.18 | 60.00  | 470.6 | 382.948500 | +22.88 | 0.000000 |
| 4  | 44 | 10.65 | 10.65 | 52.18 | 120.00 | 264.5 | 310.341000 | −14.78 | 0.000000 |
| 5  | 55 | 10.65 | 10.65 | 52.18 | 180.00 | 203.5 | 238.961000 | −14.68 | 0.000000 |
| 6  | 66 | 10.65 | 10.65 | 52.18 | 240.00 | 338.8 | 310.341000 | +9.18 | 0.000000 |
| 7  | 77 | 10.65 | 10.65 | 52.18 | 300.00 | 462.4 | 382.948500 | +20.75 | 0.000000 |
| 8  | 12 | 0.00  | 10.65 | 26.09 | 0.00   | 358.2 | 350.215700 | +2.27 | 0.000000 |
| 9  | 13 | 0.00  | 10.65 | 26.09 | 60.00  | 301.2 | 326.311900 | −7.68 | 0.000000 |
| 10 | 14 | 0.00  | 10.65 | 26.09 | 120.00 | 245.1 | 255.798600 | −4.17 | 0.000000 |
| 11 | 15 | 0.00  | 10.65 | 26.09 | 180.00 | 221.6 | 201.390100 | +10.05 | 0.000000 |
| 12 | 16 | 0.00  | 10.65 | 26.09 | 240.00 | 428.0 | 255.798600 | +67.33 | 0.000000 |

Comparison of Experiment data to Experiment surface 14.28%

TABLE 7

EXPERIMENT PARAMETERS - SCA1.NEW

| 1. TRANSDUCER (T) | A2(1) | 1 | SERIAL No. 0 | C1 400.209 um |
| 2. TRANSDUCER (R) | A2(2) | 1 | SERIAL No. 0 | C2 379.7602 um |
| 3. POLAR (T) | A2(3) | 0 | SOLID 0 deg | C3 184.1114 um |
| 4. POLAR (R) | A2(4) | 0 | SOLID 0 deg | C4 −35.7732 deg |
| 5. AZIMUTHAL (T) | A2(5) | 0 | deg | C5 73.4544 deg |
| 6. AZIMUTHAL (R) | A2(6) | 0 | deg | C6 27.6156 deg |
| 7. POSITION (T) | A2(7) | 2.54 | cm | |
| 8. POSITION (R) | A2(8) | 2.54 | cm | C7 2.8 |
| 9. EFF RADIUS (T) | A2(9) | 0.3005 | cm | |
| 10. EFF RADIUS (R) | A2(10) | 0.3005 | cm | |
| 11. Dw (T) | A2(11) | 4.95 | cm | |
| 12. A2 COEFFICIENT | A2(12) | 4.95 | | |
| 13. Df (T) | A2(13) | 0.7615 | cm | |
| 14. DELTA ATTEN | A2(14) | 55 | dB | |
| 15. Fmin | A2(15) | 2 | MHz | |
| 16. Fmax | A2(16) | 20 | MHz | |
| 17. VELOCITY (L) | A2(17) | 0.634 | cm/us | |
| 18. VELOCITY (S) | A2(18) | 0.303 | cm/us | |

TABLE 7-continued

EXPERIMENT PARAMETERS - SCA1.NEW

| | | | |
|---|---|---|---|
| 19. DENSITY | A2(19) | 4.42 | gr/cm |
| 20. IMPULSE RES AREA | A2(20) | 0 | |
| 21. WEIGHTING FAC | A2(21) | 1 | |
| 22. Re (Experiment) | A2(22) | 242.06 | Microns |
| 23. Re (Theory) | A2(23) | 264.5751 | Microns |
| INDEX OF VALUE TO CHANGE? | | | |

Documentation of Waveforms

"M9.SEQ" generates hardcopy of the scattering amplitudes obtained in the measurement, which are often useful for further analysis.

The sequences, subroutines and programs beginning with "M" make up the basic building blocks of the reconstruction software and may be operated from the multiviewing transducer data acquisition system menu. Moreover, there are many more analytical tools in the software which accommodate the needs of the research environment.

It is to be understood that the included preferred embodiment is given by way of example only, and not by way of limitation to the invention, which is solely described by the claims herein. Variations obvious to one skilled in the art will be included within the invention defined by the claims.

Following is the list of references referred to in this description:

(REFERENCES)

(1) N. Bleistein and J. K. Cohen, "Application of a new method to non-destructive evaluation", Mathematics Division, Denver Research Institute, University of Denver (1977).

(2) W. Kohn and J. R. Rice, "Scattering of long wavelength elastic waves from localized defects in solids", J. Appl. Phys. 50(5), 3353 (1979).

(3) D. O. Thompson and S. J. Wormley, "Long and intermediate wavelength flaw reconstruction", Proceedings of the Second Symposium on Energy Engineering Sciences, CONF-8404123, pp. 86–93 (1984).

(4) D. O. Thompson and S. J. Wormley, "Long and intermediate wavelength flaw reconstruction", Review of Progress in Quantitative NDE 4A, D. O. Thomopson and D. E. Chimenti, Eds., (Plenum Press, N.Y., 1985), pp. 287–296.

(5) R. B. Thompson and T. A. Gray, "A model relating ultrasonic scattering measurements through liquid-solid interfaces to unbounded medium scattering amplitudes", J. Acoust. Soc. Amer. 74(4), 1983.

(6) D. K. Hsu, J. H. Rose, and D. O. Thompson, "Reconstruction of inclusions in solids using ultrasonic Born inversion", J. App. Phys. 55(1), 1984.

(7) S. J. Wormley and D. O. Thompson, "Error sensitivity of long and intermediate wavelength flaw reconstruction", Review of Progress in Quantitative NDE 4A, D. O. Thompson and D. E. Chimenti, Eds., (Plenum Press, N.Y., 1985), pp. 203–211.

(8) D. K. Hsu, D. O. Thompson, and S. J. Wormley, "Reliability of reconstruction of arbitrarily oriented flaws using multiview transducers", submitted to IEEE Sonics and Ultrasonics, 1986.

(9) R. B. Thompson, T. A. Gray, J. H. Rose, V. Kogan, and E. F. Lopes, "The radiation of elliptical and bi-cylindrically focussed piston transducers", unpublished, submitted to J. acoust. Soc. Amer., 1986.

(10) Peter H. Rogers and A. L. Van Buren, "An exact expression for the Lommel diffraction correction integral", J. Acoust. Soc. Am. 55(4), 1974.

(11) D. O. Thompson and S. J. Wormley, "Absolute magnitude of front surface reflections in ultrasonic measurements", Review of Progress in Quantitative NDE 3A, D. O. Thompson and D. E. Chimenti, Eds., (Plenum Press, N.Y., 1984), pp. 385–393.

(12) S. J. Wormley and D. O. Thompson, "Comparison of scttering amplitudes from various transducers using diffraction and attenuation corrections", Review of Progress in Quantitative NDE 3A, D. O. Thompson and D. E. Chimenti, Eds., (Plenum Press, N.Y., 1984), pp. 323–331.

(13) J. E. Gubernatis, E. Domany, and J. A. Krumhansl, "Formal aspects of the theory of the scattering of ultrasound by flaws in elastic maerials", J. Appl. Phys. 48(7), 2804 (1977).

(14) J. E. Gubernatis, E. Domany, J. A. Krumhansl, and M. Huberman, "The Born approximation in the theory of the scattering of elastic waves by flaws", J. Appl. Phys. 48(7), 2812 (1977).

(15) J. H. Rose and J. A. Krumhansl, "Determination of flaw chracteristics from ultrasonic scattering data", J. Appl. Phys. 50(4), 2951 (1979).

(16) J. M. Richardson, "Direct and inverse problems pertaining to the scattering of elastic waves in the Rayleigh (long wavelength) regime", in Proceedings of the DARPA AFML Review of Progress in Quantitative NDE, report AFML-TR-78-205 (Air Force Wright Aeronautical Laboratories, Dayton, 1978), pp. 332–340.

(17) K. W. Fertig and J. M. Richardson, "Inverse scattering at low and intermediate frequencies", in Proceedings of the DARPA AFML Review of Progress in Quantitative NDE, report AFWAL-TR-80-4079 (Air Force Wright Aeronautical Laboratories, Dayton, 1980), pp. 528–540.

(18) J. H. Rose, R. K. Elsley, B. Tittmann, V. V. Varadan, and V. K. Varadan, "Inversion of ultrasonic scattering data", Acoustic, Electromagnetic, and Elastic Wave Scattering—Focus on the T-Matrix Approach, Pergamon Press, 1979.

(19) R. C. Addison, R. K. Elsley, and J. F. Martin, "Test bed for quantitative NDE—inversion results", Review of Progress in Quantitative NDE 1, D. O. Thompson and D. E. Chimenti, Eds., (Plenum Press, N.Y., 1982, pp. 251–261.

(20) J. H. Rose and J. L. Opsal, "The inverse Born approximation: Exact determination of shape of convex voids", Review of Progress in Quantitative 2B, D. O. Thompson and D. E. Chimenti, Eds., (Plenum Press, N.Y., 1983), pp. 949–959.

What is claimed is:

1. A non-destructive evaluation method for reconstruction of flaws in a host material utilizing an ultrasonic multi-viewing transducer data acquisition system in the long and intermediate wave lengths comprising the steps of:

placing said host material in a fluid medium;

determining the parameters of acoustic velocities of the fluid medium and host material, attenuation of the host material, and density of said host material;

detecting a flaw in the host material;

compiling information identifying the location of the flaw;

coursely positioning a transducer array by positioning means to the flaw utilizing the compiled information of the location of the flaw, the transducer array including a central transducer having a propogation axis and a plurality of perimeter transducer radially positioned around the central transducer, each having a propogation axis;

positioning the central transducer so that its axis is in alignment with a flaw in said host material by a monitoring pulse-echo operation of the center transducer;

finely positioning the plurality of perimeter transducers surrounding said central transducer so that the axes of said perimeter transducers convergingly intersect the axis of said central transducer at the position of said flaw by monitoring the pulse-echo operation of the central transducer and deriving information on the length of a path through the fluid medium between each perimeter transducer and the host material, and the depth of the flaw within the host material; and adjusting said central and perimeter transducer with adjustment means, to a desired orientation with said host material and with each other, to equalize their time path by transmitting ultrasonic pulses form the central transducer receiving the reflected pulses in the perimeter transducers, and comparing the time periods with the pulse-echo operation of the central transducer.

2. The method of claim 1 wherein there are six perimeter transducer equally spaced apart surrounding said central transducer.

3. The method of claim 1 wherein said axes of said perimeter transducers angularly intersect said axis of said central transducer at an angle between 0° and 30°.

4. The method of claim 1 wherein said central and perimeter transducers are each adjustable axially and spatially.

5. The method of claim 1 wherein each said central and perimeter transducers can be operated in any mode out of the set of transmit-only mode, receive-only mode, and transmit-and-receive mode.

6. The method of claim 5 wherein each said central and perimeter transducers can be operated both individually, and in conjunction with any of the other said transducers.

7. The method of claim 1 including the step of utilizing a computer and computer processing software for operating upon the data derived from said transducers.

8. A long and intermediate wave length ultrasonic multi-viewing transducer data acquisition means for reconstruction of flaws in a host material positioned by supporting means within a fluid medium comprising:

a plurality of transducers for obtaining flaw data from said host material each having an axis of transmission, said plurality of transducers having a central transducer and one or more perimeter transducers each with an axis of transmission angularly positioned to said axis of transmission of said central transducer, each said perimeter transducer adjustably positionable so that its said axis of transmission intersects with said host material and the axis of transmission of said central transducer;

positioning means for automatically setting the position of said plurality of transducers with respect to said host material;

an adjustment means or automatically adjusting the orientation of each perimeter transducer with respect to said center transducer;

control means to remotely control said adjustment and positioning means; and calculating means for receiving said flaw data from said transducers and identifying and reconstructing flaws in said host material.

9. The means of claim 8 further comprising a computer means connected and communicable with said plurality of transducers, said positioning means, said adjusting means, said control means, and said calculating means, to coordinate and control operation of said data acquisition means and for carrying out all control and calculating functions, including computer software programming to carry out control and operation and for operating on said flaw data to correct it, perform a regression analysis upon it, and perform an inverse Born operation upon it.

10. The device of claim 8 further comprising visualization means for visually reconstructing and preserving simulations of flaws in said host material.

* * * * *

UNITED STATES PATENT AND TRADEMARK OFFICE
CERTIFICATE OF CORRECTION

PATENT NO. : 4,817,016

DATED : March 28, 1989

INVENTOR(S) : Donald O. Thompson et al

It is certified that error appears in the above-identified patent and that said Letters Patent is hereby corrected as shown below:

Title of invention, line 5, "ACQUISTION" should read

--ACQUISITION--.

Column 1, line 5, "ACQUISTION" should read --ACQUISITION--.

Signed and Sealed this
Thirteenth Day of February, 1990

*Attest:*

JEFFREY M. SAMUELS

*Attesting Officer*     *Acting Commissioner of Patents and Trademarks*